US007829082B2

(12) United States Patent
Semba

(10) Patent No.: US 7,829,082 B2
(45) Date of Patent: Nov. 9, 2010

(54) CATHETER COMPOSITION AND USES THEREOF

(75) Inventor: Charles P. Semba, Palo Alto, CA (US)

(73) Assignee: Genentech, Inc., South San Francisco, CA (US)

(*) Notice: Subject to any disclaimer, the term of this patent is extended or adjusted under 35 U.S.C. 154(b) by 365 days.

(21) Appl. No.: 11/426,263

(22) Filed: Jun. 23, 2006

(65) Prior Publication Data

US 2006/0246050 A1 Nov. 2, 2006

Related U.S. Application Data

(62) Division of application No. 10/304,666, filed on Nov. 25, 2002, now abandoned.

(60) Provisional application No. 60/333,369, filed on Nov. 26, 2001.

(51) Int. Cl.
  *A61K 38/48* (2006.01)
  *A61K 38/49* (2006.01)
  *A61M 39/06* (2006.01)
(52) U.S. Cl. .................................. 424/94.63; 604/508
(58) Field of Classification Search ................ 604/53, 604/508; 435/69.1, 94.63
  See application file for complete search history.

(56) References Cited

U.S. PATENT DOCUMENTS

| 5,019,096 | A | 5/1991 | Fox, Jr. et al. |
|---|---|---|---|
| 5,091,442 | A | 2/1992 | Milner |
| 5,362,754 | A | 11/1994 | Raad et al. |
| 5,363,754 | A | 11/1994 | Coles et al. |
| 5,385,732 | A | 1/1995 | Anderson et al. |
| 5,399,158 | A | 3/1995 | Lauer et al. |
| 5,447,724 | A | 9/1995 | Helmus et al. |
| 5,509,896 | A | 4/1996 | Carter |
| 5,612,029 | A | 3/1997 | Bennett et al. |
| 5,688,516 | A | 11/1997 | Raad et al. |
| 5,772,640 | A | 6/1998 | Modak et al. |
| 5,824,049 | A | 10/1998 | Ragheb et al. |
| 5,837,688 | A | 11/1998 | Gelfand |
| 5,849,736 | A | 12/1998 | Wityak et al. |
| 5,865,178 | A | 2/1999 | Yock |
| 5,932,299 | A | 8/1999 | Katoot |
| 6,087,375 | A | 7/2000 | Bridon et al. |
| 6,124,277 | A | 9/2000 | Schacht et al. |
| 6,166,007 | A | 12/2000 | Sodemann |
| 6,174,537 | B1 | 1/2001 | Khan |
| 6,187,768 | B1 | 2/2001 | Welle et al. |
| 6,206,914 | B1 | 3/2001 | Soykan et al. |
| 6,231,605 | B1 | 5/2001 | Ku |
| 6,258,797 | B1 | 7/2001 | Lehner |
| 6,284,247 | B1 | 9/2001 | Goeddel et al. |
| 6,346,517 | B1 | 2/2002 | Wong et al. |
| 6,350,251 | B1 | 2/2002 | Prosl et al. |
| 2001/0021811 | A1 | 9/2001 | Yock |
| 2001/0031981 | A1 | 10/2001 | Evans et al. |
| 2002/0082582 | A1 | 6/2002 | Finch et al. |
| 2003/0206906 | A1 | 11/2003 | Semba |
| 2005/0215978 | A1 | 9/2005 | Ash |
| 2006/0257390 | A1 | 11/2006 | Semba |
| 2007/0014779 | A1 | 1/2007 | Semba |

FOREIGN PATENT DOCUMENTS

| AU | 42810/89 B | 10/1992 |
|---|---|---|
| EP | 882461 | 12/1998 |
| EP | 1040841 | 10/2000 |
| EP | 1 060 747 A2 | 12/2000 |
| EP | 1 442 753 A1 | 8/2004 |
| EP | 1 688 154 A1 | 8/2006 |
| JP | 08-503400 T | 4/1996 |
| WO | WO 94/10838 A1 | 5/1994 |
| WO | WO-95/14683 A1 | 6/1995 |
| WO | WO-98/28326 A1 | 7/1998 |
| WO | WO-00/53264 A1 | 9/2000 |
| WO | WO 01/85249 | 11/2001 |
| WO | WO-03/045466 A2 | 6/2003 |
| WO | WO-03/045466 A3 | 6/2003 |
| WO | WO-2006/049813 A2 | 5/2006 |
| WO | WO-2006/049813 A3 | 5/2006 |
| WO | WO-2008/070353 A2 | 6/2008 |
| WO | WO-2008/070353 A3 | 6/2008 |

OTHER PUBLICATIONS

Antani, M.R., "Catheter-directed thrombolysis for the treatment of acute deep venous thrombosis" *Supplement to Applied Radiology* pp. 29-35 (Jul. 2001).
Ashton, J., et al., "Effects of heparin versus saline solution on intermittent infusion device irrigation" *Heart & Lung: Journal of Critical Care* 19(6): 608-612 (Nov. 1990).
Boorgu et al., "Adjunctive Antibiotic/Anticoagulant Lock Therapy in the Treatment of Bacteremia Associated with the Use of a Subcutaneously Implanted Nemodialysis Access Device." *ASAIO J.* 46:767-770 (Nov. 2000).
Buturovic et al., "Filling Hemodialysis Catheters in the Interdialytic Period: Heparin Versus Citrate Versus Polygeline: A Prospective Randomized Study" *Artificial Organs* 22:945-947 (1998).
Darouiche and Raad, "Prevention of Catheter-Related Infections: The Skin" *Nutrition* (Suppl.) 13(4):26S-29S (1997).

(Continued)

*Primary Examiner*—Manjunath N Rao
*Assistant Examiner*—Marsha M. Tsay
(74) *Attorney, Agent, or Firm*—Morrison & Foerster LLP

(57) ABSTRACT

A composition useful for removal of fibrin-bound blood clots from a catheter comprises water, a fibrinolytically effective amount of a plasminogen activator, and a preservatively effective amount of a bacteriostatic organic alcohol. The composition does not comprise a chelating agent.

7 Claims, 1 Drawing Sheet

OTHER PUBLICATIONS

Food and Drug Administration, "FDA Issues Warning on Tricitrasol Dialysis Catheter Anticoagulant" *FDA Talk Paper T00-16* (Apr. 14, 2000).

Garrelts, James C., et al., "Comparison of heparin and 0.9% sodium chloride injection of indwelling intermittent i.v. devices" *Clinical Pharmacy* 8:34-39 (Jan. 1989) Abstract.

Greco et al., "Patency of a Small Vessel Prosthesis Bonded to Tissue Plasminogen Activator and Iloprost." *Ann. Vasc. Surg.* 9(2): 140-145 (1995).

Haire et al., "Urokinase Versus Recombinant Tissue Plasminogen Activator in Thrombosed Central Venous Catheters: A Double-Blinded, Randomized Trial" *Thromb. Haemost.* 72:543-547 (1994).

Henrickson et al., "Prevention of Central Venous Catheter-Related Infections and Thrombotic Events in Immunocompromised Children by the Use of Vancomycin/Ciprofloxacin/Heparin Flush Solution: A Randomized, Multicenter, Double-Blind Trial" *J. Clin. Oncol.* 18:1269-1278 (2000).

Kamal et al., "Reduced Intravascular Catheter Infection by Antibiotic Bonding: A Prospective Randomized, Controlled Trial" *J. Amer. Med. Assc.* 265:2364-2368 (May 1991).

Karaaslan, H., et al., "Risk of heparin lock-related bleeding when using indwelling venous catheter in haemodialysis" *Nephrol Dial Transplant* 16:2072-2074 (2001).

Karnes, H. T. et al., "Benzyl Alcohol Interference from Heparin Lock Flush Solutions in a High Pressure Liquid Chromatographic Procedure for Mezlocillin" *Therapeutic Drug Monitoring*, New York:Raven Press, Ltd. vol. 9(4):456-460 (1987).

Lokich et al., "Complications and Management of Implaned Venous Access Catheters." *J. Clin. Oncol.* 3:710-717 (1985).

Ouriel at al., "Comparison of streptokinase, urokinase, and recombinant tissue plasminogen activator in an in vitro model of venous thrombolysis" *Journal of Vascular Surgery* 22:593-597 (Nov. 1995).

Patel et al., "Successful Use of Low Dose r-Hirudin (Refludan)for Recurrent Dialysis Catheter Thrombosis in a Patient with Heparin Induced Thrombocytopenia." *Thromb. Haemost.* 82:1205-1206 (1999).

Purchase and Gault., "Hemodialysis with a Permcath Kept Open with Streptokinase and Later Citrate in a Heparin-Sensitive Patient." *Nephron* 58:119-120 (1991).

Root at al., "Inhibitory Effect of Disodium EDTA Upon the Growth of Staphylococcus epidermidis In Vitro: Relation to Infection Prophylaxis of Hickman Catheters." *Antimicrob. Agents Chemother.* 32:1627-1631 (Nov. 1988).

Rubin., "Local Installation of Small Doses of Streptokinase for Treatment of Thrombotic Occlusions of Long-Term Access Catheters." *J. Clin. Oncol.* 1:572-573 (Sep. 1983).

Schenk et al., "Recombinant Tissue Plasminogen Activator is a Useful Alternative to Heparin in Priming Quinton Permeath." *Amer. J. Kidney Diseases* 35:130-136 (Jan. 2000).

Schwartz et al., "Prevention of Bacteremia Attributed to Luminal Colonization of Tunneled Central Venous Catheters With Vancomycin-Susceptible Organisms." *J. Clin. Oncology* 8:1591-1597 (Sep. 1990).

Skrzydlewska, E., Worowski, Krzysztof, "Effect of ethanol and acetaldehyde on fibrinolytic system in vitro" *Roczniki Akademii Medyczne w Bialymstoku* 29-30:163-173 (-1985 1984).

Sodemann et al., "Gentamicin/Sodium-Citrate Mixture as Antibiotic-Lock Technique for Salvage and Prevention of Catheter-Related Infections- A Four Year Trial." *30th Annual Meeting of American Society of Nephrology*, San Antonio, TX (A0811, S064 (PS)) pp. 173A (Nov. 2-5, 1997).

Sodemann et al., "Two Years' Experience with Dialock and CLS (A New Antimicrobial Lock Solution)" *Blood Purif.* 19:251-254 (2001).

Stas et al., "Trisodium Citrate 30% vs Heparin 5% as Catheter Lock in the Interdialytic Period in Twin- or Double-Lumen Dialysis Catheters for Intermittent Haemodialysis." *Nephrol. Dial. Transplant. Purif.* 19:251-254 (2001).

Tang, M., "Bacteriostatic Saline Flush Interferes with Sodium Measurement on the Ektachem 700" *Clinical Chemistry* 39(9):2032 (1993).

Vercaigne et al., "Antibiotic-Heparin Lock: In Vitro Antibiotic Stability Combined with Heparin in a Central Venous Catheter." *Pharmcotherapy* 20(4):394-399 (Apr. 2000).

Wiernikowski et al., "Bacterial Colonization of Tunneled Right Atrial Catheters in Pediatric Oncology: A Comparison of Sterile Saline and Bacteriostatic Saline Flush Solutions." *Am. J. Pediat. Hematol. Oncol.* 13:137-140 (1991).

Woodhouse et al., "Lysis of Surface-Localized Fibrin Clots by Absorbed Plasminogen in the Presence of Tissue Plasminogen Activator." *Biomaterials* 17:75-77 (1996).

Zhou et al., "Development of a Multiple-Drug Delivery Implant for Intraocular Management of Proliferative Vitreoretinopathy." *J. Controlled Release* 55:281-295 (1998).

Abbas, A.E. et al. (Sep. 6, 2005). "Intracoronary Fibrin-Specific Thrombolytic Infusion Facilities Percutaneous Recanalization of Chronic Total Occlusion," *Journal of the American College of Cardiology* 46(5):793-798.

Anonymous. (2005). U.S. Renal Data System, USRDS 2005 Annual Data Report: Atlas of End-Stage Renal Disease in the United States, National Institutes of Health, *National Institute of Diabetes and Digestive and Kidney Diseases*, Bethesda, MD, 6-parts, 282 pages.

Arepally, A. et al. (Jan. 2002). "Weight-Based rt-PA Thrombolysis Protocol for Acute Native Arterial and Bypass Graft Occlusions," *J. Vasc. Interv. Radiol.* 13(1):45-50.

Falk, A. et al. (Jun. 30, 2005). "Tenecteplase in the Treatment of Thrombosed Hemodialysis Grafts," *Cardiovascular and Interventional Radiology* 28(4):472-475.

Refino, C.J. et al. (1993). "A Variant of Tissue Plasminogen Activator (T103N, N117Q, KHRR 296-299 AAAA) With a Decreased Plasma Clearance Rate is Substantially More Potent Than Activase® rt-PA in a Rabbit Thrombolysis Model," *Thromb. Haemost.* Abstracts Edition 69(6):841.

Allwood, M.C. (1999). "Problems With Lines and the Pharmacist's Role," *Nutrition* 15(3):252-253.

Budavari, S. et al. eds. (1996). *The Merck Index*, Merck & Co., Inc.: Whitehouse Station, NJ, p. 189.

El-Kassimi, F.A. et al. (Oct. 1986). "Adult Respiratory Distress Syndrome and Disseminated Intravascular Coagulation Complicating Heat Stroke," *Chest* 90(4):571-574.

Hardaway, R.M. et al. (Oct. 2001). "A Shock Toxin That Produces Disseminated Intravascular Coagulation and Multiple Organ Failure," *The American Journal of the Medical Sciences* 322(4):222-228.

Merriam-Webster (2009). OnLine Definition of "Expose" located at <http://mwl.merriam-webster.com/dictionary/expose>, last visited Dec. 7, 2009, two pages.

Non-Final Office Action mailed Dec. 23, 2009, for U.S. Appl. No. 11/533,305, filed Sep. 19, 2006, nine pages.

Ponec, D. et al. (Aug. 2001). "Recombinant Tissue Plasminogen Activator (Alteplase) for Restoration of Flow in Occluded Central Venous Access Devices: A Double-Blind Placebo-Controlled Trial—The Cardiovascular Thrombolytic to Open Occluded Lines (COOL) Efficacy Trial," *J. Vasc. Interv. Radiol.* 12:951-955.

Valji, K. et al. (Jun. 1995). "Pulse-Spray Pharmacomechanical Thrombolysis of Thrombosed Hemodialysis Access Grafts: Long-Term Experience and Comparison of Original and Current Techniques," *AJR* 164:1495-1500.

Allie, D. et al. (Sep. 24, 2002). "Novel Combination Thrombolytic Therapy in Limb Salvage: Mechanical Thrombectomy (Rheolytic Thrombectomy with Angiojet) and Chemical Thrombolysis (Tenecteplase) 'Power-Pulse Spray' Technique," *Am. J. Cardiol.* 90:108H, Poster Abstract No. TCT-270.

Allie, D.E. et al. (Mar. 2003). "Tenecteplase in Peripheral Thrombolysis: Initial Safety and Feasibility Experience," presented at *Society of Intervention Radiology*, p. S17, Abstract No. 48.

Anonymous. (2002). "Cathflo Activase®. Full Prescribing Information," in *2002 Physicians Desk Reference*, Thomas Medical Economics Co.: Montvale, NJ, p. 3611-3612.

Anonymous. (2002). "Retavase®. Full Prescribing Information," in *2002 Physicians Desk Reference*, Thomas Medical Economics Co.: Montvale, NJ, pp. 1182-1184.

Anonymous. (2002). "Streptase®. Full Prescribing Information," in *2002 Physicians Desk Reference*, Thomas Medical Economics Co.: Montvale, NJ, pp. 647-649.

Anonymous. (2002). "TNKase™. Full Prescribing Information," in *2002 Physicians Desk Reference*, Thomas Medical Economics Co.: Montvale, NJ, three pages.

Assent-2 Investigators. (Aug. 28, 1999). "Single-Bolus Tenecteplase Compared with Front-Loaded Alteplase in Acute Myocardial Infarction: The ASSENT-2 Double-Blind Randomised Trial. Assessment of the Safety and Efficacy of a New Thrombolytic Investigators," *Lancet* 354:716-722.

Azmi-Ghadimi, H. et al. (Feb. 2002). "Use of Intraventricular Tissue Plasminogen Activator and Guglielmi Detachable Coiling for the Acute Tratment of Casted Ventricles from Cerebral Aneurysm Hemorrhage: Two Technical Case Reports," *Neurosurgery* 50(2):421-424.

Benedict, C.R. et al. (Nov. 15, 1995). "New Variant of Human Tissue Plasminogen Activator (TPA) with Enhanced Efficacy and Lower Incidence of Bleeding Compared with Recombinant Human TPA," *Circulation* 92(10):3032-3040.

Bookstein, J.J. et al. (Mar. 2000). "Augmented Experimental Pulse-Spray Thrombolysis with Tissue Plasminogen Activator, Enabling Dose Reduction by One or More Orders of Magnitude," *J. Vasc. Interv. Radiol.* 11(3):299-303.

Bookstein, J.J. et al. (Nov.-Dec. 2000). "Plasminogen-Enriched Pulse-Spray Thrombolysis with tPA: Further Developments," *J. Vasc. Interv. Radiol.* 11(10):1353-1362.

Burkart, D.J. et al. (Nov. 2002). "Thrombolysis of Occluded Peripheral Arteries and Veins with Tenecteplase: A Pilot Study," *J. Vasc. Interv. Radiol.* 13(11):1099-1102.

Burkart, D.J. et al. (Jun. 2003). "Thrombolysis of Acute Peripheral Arterial and Venous Occlusions with Tenecteplase and Eptifibatide: A Pilot Study," *J. Vasc. Interv. Radiol.* 14(6):729-733.

Cairoli, O.M. (Mar. 2002). "Practical Application: Using Tissue Plasminogen Activator Overnight in Catheter Clearance on Tunnel Catheters Used for Hemodialysis," *Proceedings of the 22$^{nd}$ Annual Conference on Dialysis* 22(Suppl. 1):S56.

Calis, K.A. et al. (Oct. 15, 1999). "Bioactivity of Cryopreserved Alteplase Solutions," *Am. J. Health-Syst. Pharm.* 56:2056-2057.

Casteneda, F. et al. (Jun. 2002). "Catheter-Directed Thrombolysis in Deep Venous Thrombosis with Use of Reteplase: Immediate Results and Complications from a Pilot Study," *J. Vasc. Interv. Radiol.* 13(6):577-580.

Chang, R. et al. (Feb. 2001). "Daily Catheter-Directed Single Dosing of t-PA in Treatment of Acute Deep Venous Thrombosis of the Lower Extremity," *J. Vasc. Interv. Radiol.* 12(2):247-252.

Collen, D. et al. (1994). "Comparative Thrombolytic Properties of Tissue-Type Plasminogen Activator and of a Plasminogen Activator Inhibitor-1-Resistant Glycosylation Variant, in a Combined Arterial and Venous Thrombosis Model in the Dog," *Thromb. Haemost.* 72(1):98-104.

Cornelius, R.M. et al. (2000). "Adsorption of Proteins from Infant and Adult Plasma to Biomaterial Surfaces," *J. Biomed. Meter. Res.* 15:622-632.

Daeihagh, P. et al. (Jul. 2000). "Efficacy of Tissue Plasminogen Activator Administration on Patency of Hemodialysis Access Catheters," *American Journal of Kidney Diseases* 36(1):75-79.

Davidian, M.M. et al. (Mar. 2000). "Initial Results of Reteplase in the Treatment of Acute Lower Extremity Arterial Occlusions," *J. Vasc. Interv. Radiol.* 11(3):289-294.

Dawson, K.M. et al. (Jun. 10, 1994). "Plasminogen Mutants Activated by Thrombin. Potential Thrombus-Selective Thrombolytic Agents," *J. Biol. Chem.* 269(23):15989-15992.

Decrinis, M. et al. (1993). "A Simplified Procedure for Intra-arterial Thrombolysis with Tissue-Type Plasminogen Activator in Peripheral Arterial Occlusive Disease: Primary and Long-Term Results," *European Heart Journal* 14:297-305.

Dowling, K. et al. (Mar.-Apr. 2004). "The Use of Tissue Plasminogen Activator Infusion to Re-establish Function of Tunneled Hemodialysis Catheters," *Nephrology Nursing Journal* 31(2):199-200.

Drescher, P. et al. (Jan. 2002). "Initial Experience with the Combination of Reteplase and Abciximab for Thrombolytic Therapy in Peripheral Arterial Occlusive Disease: A Pilot Study," *J. Vasc. Interv. Radiol.* 13(1):37-43.

Drugbank Accession No. BTD00019 "Tenecteplase," last updated Feb. 1, 2007, located at <http//redpoll.pharmacy.ualberta.ca/drugbank/cgi-bin/getCard.cgi?CARD=BTD00019.txt>, last visited Feb. 15, 2007, six pages.

Elsharawy, M. et al. (Sep. 2002). "Early Results of Thrombolysis vs Anticoagulation in Iliofemoral Venous Thrombosis. A Randomized Clinical Trial," *Eur. J. Vasc. Endovasc. Surg.* 24:209-214.

Eyrich, H. et al. (Aug. 1, 2002). "Alteplase Versus Urokinase in Restoring Blood Flow in Hemodialysis-Catheter Thrombosis," *Am. J. Health-Syst. Pharm.* 59:1437-1440.

Final Office Action mailed Aug. 24, 2007, for U.S. Appl. No. 10/697,142, filed Oct. 30, 2003, ten pages.

Final Office Action mailed Feb. 5, 2009, for U.S. Appl. No. 10/697,142, filed Oct. 30, 2003, ten pages.

Findlay, J.M. et al. (May 1991). "Lysis of Intraventricular Hematoma with Tissue Plasminogen Activator," *J. Neurosurg.* 74:803-807.

Gibson, S.P. et al. (1991). "Five Years Experience with the Quinton Permcath for Vascular Access," *Nephrology Dialysis Transplantation* 6:269-274.

Graul, A. et al. (1997). "Xemilifiban" *Drugs of the Future* 22(5):508-517.

Habowski, S.R. et al. (2000). "Use of Tissue Plasminogen Activator (t-Pa) for Hemodialysis Catheter Malfuntion," *J. Am. Soc. Nephrol.* 11:185A, Abstract No. A0988, Poster SA571 (PS).

Hammes, M.S. et al. (2001). "Intraluminal Alteplase (t-Pa) Is an Effective Means to Treat Occluded Hemodialysis (HD) Catheters," *J. Am. Soc. Nephrol.* 12:290A, Abstract No. A1487, Poster SU1-0723 (PS).

Hara, T. et al. (1994). "DX-9065a; A New Synthetic, Potent Anticoagulant and Selective Inhibitor for Factor Xa," *Thromb. Haemost.* 71(3):314-319.

Hofmann, L.V. et al. (2001, e-pub. Nov. 8, 2001). "GPIIb-IIIa Receptor Inhibitors: What The Interventional Radiologist Needs to Know," *Cardiovasc. Interv. Radiol.* 24:361-367.

International Search Report mailed Aug. 4, 2003, for PCT/US02/37878, filed Nov. 25, 2002, one page.

International Search Report mailed Jun. 25, 2008, for PCT/US2007/082933, filed Oct. 30, 2007, four pages.

Kaiser, B. (1998). "Thromblin and Factor Xa Inhibitors," *Drugs of the Future* 23(4):423-436.

Kawasaki, T. et al. (1998). "Effect of a Synthetic Factor Xa Inhibitor, YM-60828, on Blood Vessel Patency in Combination with a Thrombolytic Agent and on Blood Loss from the Operation Site in a Rat Model of Arterial Thrombosis," *Thromb. Haemost.* 79:859-864.

Keyt, B.A. et al. (Apr. 1994). "A Faster-Acting and More Potent Form of Tissue Plasminogen Activator," *Proc. Natl. Acad. Sci. USA* 91:3670-3674.

Leblang, S.D. et al. (Aug. 1992). "Low-Dose Urokinase Regimen for the Treatment of Lower Extremity Arterial and Graft Occlusions: Experience in 132 Cases," *J. Vasc. Interv. Radiol.* 3(3):475-483.

Little, M.A. et al. (Jan. 2002). "A Longitudinal Study of the Repeated Use of Alteplase as Therapy for Tunneled Hemodialysis Catheter Dysfunction," *American Journal of Kidney Diseases* 39(1):86-91.

McNamara, T.O. et al. (Apr. 1985). "Thrombolysis of Peripheral Arterial and Graft Occlusions: Improved Results Using High-Dose Urokinase," *Am. J. Radiol.* 144:769-775.

McNamara, T.O. et al. (Sep. 22, 1999). "Bleeding Associated with Intrathrombus Infusions of r-tPA for Peripheral Arterial and Venous Occlusions," *Am. J. Cardiol.* 84:37P, Abstract No. TCT-92.

Merriam-Webster OnLine Definition of "Dwell" located at http://mwl.merriam-webster.com/dictionary/dwell, last visited Aug. 13, 2007, one page.

Mewissen, M.W. et al. (Apr. 1999). "Catheter-Directed Thrombolysis for Lower Extremity Deep Venous Thrombosis: Report of a National Multicenter Registry," *Radiology* 211(1):39-49.

Moss, A.H. et al. (Dec. 1988). "Use of a Silicone Catheter With a Dacron Cuff for Dialysis Short-Term Vascular Access," *American Journal of Kidney Diseases* XII(6):492-498.

National Kidney Foundation. (2001). "K/DOQI Clinical Practice Guidelines for Vascular Access, 2000," *Am. J. Kidney Dis.* 37(Suppl. 1):S137-S181.

Nehme, T.N. et al. (2002). "Tenecteplase for the Lyse and Wait Technique in Recnalization of Thrombosed PTFE Hemodialysis Grafts," Poster No. 320, *J. Vasc. Interv. Radiol.* 13:S109.

Non-Final Office Action mailed Mar. 13, 2007, for U.S. Appl. No. 10/697,142, filed Oct. 30, 2003, six pages.

Non-Final Office Action mailed Jun. 6, 2008, for for U.S. Appl. No. 10/697,142, filed Oct. 30, 2003, nine pages.

O'Mara, N. B. et al. (2000). "tPA for Central Vein Dialysis Catheter Patency," *J. Am. Soc. Nephrol.* 11:292A, Abstract No. A1530.

Ouriel, K. et al. (Apr. 16, 1998). "A Comparison of Recombinant Urokinase with Vascular Surgery as Initial Treatment for Acute Arterial Occlusion of the Legs," *New England J. of Medicine* 338(16):1105-1111.

Ouriel, K. et al. (Mar. 2000). "Complications Associated with the Use of Urokinase and Recombinant Tissue Plasminogen Activator for Catheter-Directed Peripheral Arterial and Venous Thrombolysis," *J. Vasc. Interv. Radiol.* 11(3):295-298.

Ouriel, K. et al. (Jul.-Aug. 2000). "Reteplase in the Treatment of Peripheral Arterial and Venous Occlusions: A Pilot Study," *J. Vasc. Interv. Radiol.* 11(7):849-854.

Patel, N. et al. (May 2001). "SCVIR Reporting Standards for the Treatment of Acute Limb Ischemia with Use of Transluminal Removal of Arterial Thrombus," *J. Vasc. Interv. Radiol.* 12(5):559-570.

Razavi, M.K. et al. (2002). "Initial Clinical Results of Tenecteplase (TNK) in Catheter-Directed Thrombolytic Therapy," *J. Endovasc. Ther.* 9:593-598.

Razavi, M.K. et al. (Feb. 2002). "Initial Clinical Results of Tenecteplase (TNK) in Catheter-Directed Thrombolytic Therapy," presented Apr. 7, 2002, at the 27th Annual Meeting of the Society of Cardiovascular Interventional Radiology, *J. Vasc. Interv. Radiol.* 13(2-part 2):S11, Abstract No. 29.

Refino, C.J. et al. (1993). "A Variant of Tissue Plasminogen Activator (T103N, N117Q, KHRR 296-299 AAAA) With a Decreased Plasma Clearance Rate is Substantially More Potent Than Activase® rt-PA in a Rabbit Thrombolysis Model," *Thromb. Haemost. Abstracts Edition* 69(6):841.

Ricotta, J.J. et al. (Jul. 1987). "Use and Limitations of Thrombolytic Therapy in the Treatment of Peripheral Arterial Ischemia: Results of a Multi-Institutional Questionnaire," *J. Vasc. Surg.* 6(1):45-50.

Roberts, N. E. et al. (2000). "Outpatient Use of Alteplase (t-PA) in De-Clotting Dialysis Catheters," *J. Am. Soc. Neprol.* 11:195A, Abstract No. A1040.

Scarborough, R.M. et al. (1998). "Eptifibatide," *Drugs of the Future* 23(6):585-590.

Sandbaek, G. et al. (1999). "Soluble, Thrombin-Related Material in Arterial Thrombi and Plasma Studied During Catheter-Directed Intra-Arterial Thrombolysis," *Blood Coagulation and Fibrinolysis* 10(2):87-91.

Semba, C.P. et al. (May 1994). "Iliofemoral Deep Venous Thrombosis: Aggressive Therapy with Catheter-Directed Thrombolysis," *Radiology* 191(2):487-494.

Semba, C.P. et al. (Feb. 2000). "Thrombolytic Therapy with Use of Alteplase (rt-PA) in Peripheral Arterial Occlusive Disease: Review of the Clinical Literature," *J. Vasc. Interv. Radiol.* 11(2):149-161.

Semba, C.P. et al. (Mar. 2000). "Alteplase as an Alternative to Urokinase," *J. Vasc. Interv. Radiol.* 11(3):279-287.

Semba, C.P. et al. (Jun. 2001). "Alteplase and Tenecteplase: Applications in the Peripheral Circulation," *Tech. Vasc. Interv. Radiol.* 4(2):99-106.

Semba, C.P. et al. (Feb. 2002). "Alteplase Stability and Bioactivity After Thrombolysis-Facilitated Rheolytic or High-Speed Maceration Thrombectomy," presented Apr. 11, 2002, at the 27th Annual Meeting of the Society of Cardiovascular Interventional Radiology, *J. Vasc. Interv. Radiol.* 13(2-Part 2):S76.

Semba, C.P. et al. (Feb. 2002). "Tenecteplase (TNK): Protein Stability and Bioactivity of Thawed or Diluted Solutions Used in Peripheral Thrombolysis," presented Apr. 11, 2002, at the 27th Annual Meeting of the Society of Cardiovascular Interventional Radiology, *J. Vasc. Interv. Radiol.* 13(2-Part 2):575, Abstract No. 218.

Semba, C.P. et al. (Apr. 2003). "Tenecteplase: Stability and Bioactivity of Thawed or Diluted Solutions Used in Peripheral Thrombolysis," *J. Vasc. Interv. Radiol.* 14(4):475-479.

Shortell, C.K. et al. (Nov. 2001). "Safety and Efficacy of Limited-Dose Tissue Plasminogen Activator in Acute Vascular Occlusion," *J. Vasc. Surg.* 34(5):854-859.

Spry, L.A. et al. (Jan. 2001). "Low-Dose tPA for Hemodialysis Catheter Clearance," *Dialysis and Transplantation* 30(1):10-13.

STILE Investigators. (Sep. 1994). "Results of a Prospective Randomized Trial Evaluating Surgery Versus Thrombolysis for Ischemia of the Lower Extremity, The STILE Trial," *Ann. Surg.* 220(3):251-268.

Suggs, W.D. et al. (Aug. 1999). "When is Urokinase Treatment an Effective Sole or Adjunctive Treatment for Acute Limb Ischemia Secondary to Native Artery Occlusion," *Am. J. Surg.* 178:103-106.

Suhocki, P.V. et al. (Sep. 1996). "Silastic Cuffed Catheters for Hemodialysis Vascular Access: Thrombolytic and Mechanical Correction of Malfunction," *American Journal of Kidney Diseases* 28(3):379-386.

Supplemental Partial European Search Report mailed Dec. 30, 2005, for EP Patent Application No. 02791318.5, four pages.

Swischuk, J.L. et al. (Apr. 2001). "Transcatheter Intraarterial Infusion of rt-PA for Acute Lower Limb Ischemia: Results and Complications," *J. Vasc. Interv. Radiol.* 12(4):423-430.

Sze, D.Y. et al. (Dec. 2001). "Treatment of Massive Pulmonary Embolus with Catheter-Directed Tenexteplase," *J. Vasc. Interv. Radial.* 12(12):1456-1457.

Thomas, S.M. et al. (1999). "Avoiding the Complications of Thrombolysis," *Br. J. Surg.* 86:710.

Valji, K. et al. (Apr. 2000). "Evolving Strategies for Thrombolytic Therapy of Peripheral Vascular Occlusion," *J. Vasc. Interv. Radiol.* 11(4):411-420.

Verstraete, M. (Jul. 2000). "Third-Generation Thrombolytic Drugs," *Am. J. Med.* 109:52-58.

Yamazaki, M. et al. (1994). "Effects of DX-9065a, an Orally Active, Newly Synthesized and Specific Inhibitor of Factor Xa, Against Experimental Disseminated Intravascular Coagulation in Rats," *Thromb. Haemost.* 72(3):393-396.

Zacharias, J.M. et al. (Jan. 2003). "Alteplase Versus Urokinase for Occluded Hemodialysis Catheters," *The Annals of Pharmaotherapy* 37:27-33.

Buchman, A.L. at al. (Jan. 2001). "Complications of Long-Term Home Total Parenteral Nutrition," *Digestive Diseases and Sciences* 46(1):1-18.

Refino, C.J. et al. (1993). "A Variant of t-PA (T103N, KHRR 296-299 AAAA) that, by Bolus, Has Increased Potency and Decreased Systemic Activation of Plasminogen," *Thromb. Haemost.* 70(2):313-319.

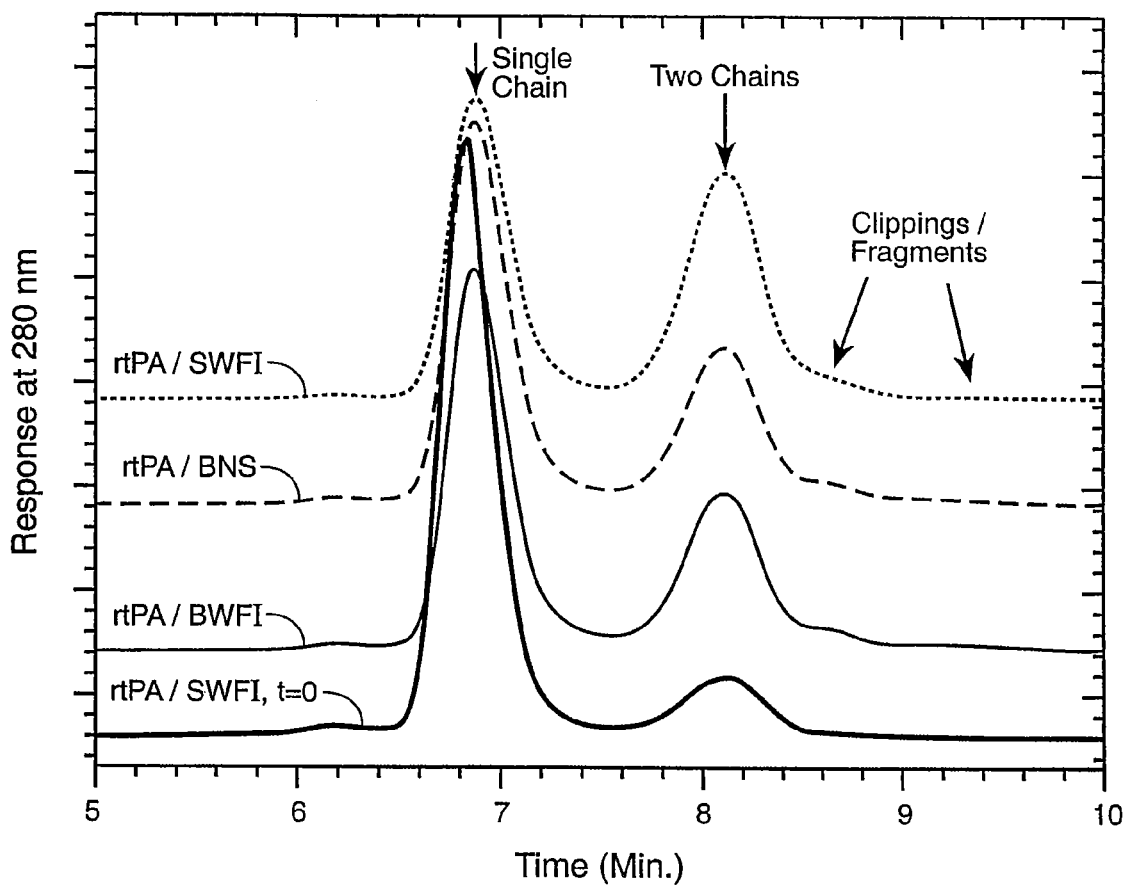
*FIG._1*

CATHETER COMPOSITION AND USES THEREOF

RELATED APPLICATIONS

This application is a divisional application of U.S. application Ser. No. 10/304,666, filed Nov. 25, 2002 now abandoned, claiming priority under 35 USC 119(e) to provisional application No. 60\333,369 filed Nov. 26, 2001, the contents of which are incorporated herein by reference.

BACKGROUND OF THE INVENTION

1. Field of the Invention

The present invention relates to the field of indwelling medical devices, in particular catheters, as well as to the field of methods and compositions for flushing, locking, priming, and coating these medical devices. The invention also relates to pharmaceutical preparations useful in increasing catheter flow and preventing infection in catheters with the potential for fibrin deposition or with preexisting fibrin-bound clots.

2. Description of Related Disclosures

Delivery systems are widely used in medicine as a means for introducing liquid material that might include medicaments, nutrition, or other active agents to a particular locus in a patient. Such systems frequently involve the use of catheters, which, for many applications, are surgically or intravenously located and stitched into place for long-term administration of the desired material. Typical systems include central catheters such as may be used for total parenteral nutrition (TPN) used in, e.g., short bowel syndrome (for the duration of life), with the risk of sepsis or endocarditis. Such systems also include catheters and drains that are involved in peritoneal dialysis for those with terminal kidney failure, which, if infected, can lead to peritonitis with serious consequences.

Intravascular catheters are among the most commonly used medical devices. Such catheters are routinely placed into a patient's vascular system for many procedures and often are left in place for extended periods. One type of delivery system used for some years in the treatment of conditions in humans comprises a reservoir or chamber of small volume subcutaneously implanted under the fascia having direct access via a catheter to the cardiovascular system. Such systems are known as port systems. Since a port and an intravascular catheter are direct paths from the outside environment to the patient's bloodstream, the presence of the catheter or port presents a substantial and continuous potential for introduction of microorganisms into the patient's bloodstream.

It is now generally acknowledged that indwelling catheterization in medical, surgical, gynecological, urological and other patients can lead to serious infection of the urogenital tract. Practitioners have developed many protocols related to placement, use, attachment and detachment of fluid-handling devices and other procedures related to catheters. The goal of almost all of these procedures is to avoid introduction of a microorganism into the patient's bloodstream.

A number of methods for reducing the risk of infection have been developed that incorporate anti-infective agents into medical devices, none of which have been clinically proven to be completely satisfactory. Such devices desirably provide effective levels of anti-infective agent during the entire period that the device is being used. This sustained release may be problematic to achieve, in that a mechanism for dispersing anti-infective agent over a prolonged period of time may be required, and the incorporation of sufficient amounts of anti-infective agent may adversely affect the surface characteristics of the device. The difficulties encountered in providing effective anti-microbial protection increase with the development of drug-resistant pathogens.

The current standard care of vascular catheters includes flushing the lumen of the catheter with an anti-coagulant, such as heparin, to prevent blood in and around the tip of the catheter from coagulating and obstructing the flow of fluids through the catheter. Furthermore, heparin has no anti-microbial activity, and, in addition, if not carefully controlled, it can carry the anti-coagulation process too far, thereby presenting a risk of hemorrhage. Heparin can also result in antibody formation, leading to a serious autoimmune condition of heparin-induced thrombocytopenia (HIT), which depletes platelets and further increases risk of bleeding. Thus, infections, as well as thrombotic occlusion, continue to occur frequently despite the prophylactic use of heparin flushes. Knowledge of the pathogenesis and microbiology of central venous catheter-related infections is essential to provide effective prevention of this problem.

*Staphylococcus epidermidis* and *S. aureus* account for 75% of central venous catheter (CVC)-related infections. *Candida* species account for another 10% to 15% of such infections. The use of anti-*staphylococcal* antibiotics to prevent these infections has been found to reduce CVC-related bacterial infections, but only at the expense of the occurrence of higher rates of fungal (*Candida*) infections.

There is also an observed correlation between thrombogenesis and infection. Essentially, a fibrin sheath that subsequently acts to cover the internal and external surfaces of a catheter engulfs indwelling vascular catheters. This fibrin sheath provides such organisms as *Staphylococci* and *Candida* with an enhanced adherence capacity to the catheter surface. Unlike these particular microbes, gram-negative bacilli do not adhere well to fibrin and fibronectin. A composition that halted fibrin formation would thus be particularly useful in preventing the colonization of *Staphylococci, Candida,* and the like, at indwelling catheter sites.

When a medicament is introduced into a patient through a catheter, the practitioner commonly follows the introduction with a flush solution that may include an anticoagulant such as heparin. The purpose of the flush solution is to move the medicament out of the catheter so that the entire dosage is delivered, and to leave a residual fill in the catheter so that the patient's blood does not back up in the catheter and possibly form a clot that would occlude the bore of the catheter. Thus, when the catheter is subsequently needed again, the properly flushed catheter is likely fully patent and ready for the next usage.

Root et al., *Antimicrob. Agents Chemother.*, 32: 1627-1631 (1988) published a study that reported on the effect in catheters of disodium ethylene diamine tetraacetic acid (EDTA), a compound well known for its chelating properties in vivo and widely used as an anticoagulant in vitro. U.S. Pat. No. 5,363,754 disclosed that pharmaceutical compositions of a mixture of minocycline and EDTA were useful in maintaining the patency of a catheter port. U.S. Pat. No. 5,091,442 described tubular articles, such as condoms and catheters, which are rendered anti-microbially effective by the incorporation of a non-ionic sparingly soluble anti-microbial agent, such as triclosan. The anti-microbial agent may be distributed throughout the article, or in a coating thereon. U.S. Pat. No. 5,362,754 disclosed a pharmaceutical preparation that includes minocycline and EDTA for maintaining the patency of a catheter. U.S. Pat. No. 5,362,754 reported the use of a mixture of minocycline and EDTA (M-EDTA) to maintain the patency of a catheter port.

Purchase et al., *Nephron*, 58: 119-20 (1991) disclosed use of calcium chelators, including citrate, for this purpose. Butuovic et al., *Artif. Organs.* 22: 945-7 (1998) disclosed that citrate and polygeline, which is a plasma substitute made from cow bones, were equally as effective as heparin in maintaining the catheter. In a talk presented at the 30th annual meeting of the American Society of Nephrology, held Nov. 2-5, 1997 in San Antonio, Tex., Sodemann et al. reported that the replacement of catheters due to infection can be avoided by routine application of the concentrated gentamicin/citrate mixture.

However, one citrate calcium chelator for dialysis catheters, designated TRICITRASOL™, has certain drawbacks. Some patients reported dysgensia for a short period immediately after the injection of citrate. Recently the FDA reported a case of a patient who died shortly after the injection of citrate as a catheter lock (Stas et al., *Nephrol Dial Transplant*, 16: 1521-1522 (2001); FDA issues warning on triCitrasol (trademark) dialysis catheter anticoagulant. FDA Talk Paper T00-16, 14 April 2000.

U.S. Pat. No. 5,019,096 disclosed infection-resistant medical devices comprising a synergistic combination of a silver salt (such as silver sulfadiazine) and chlorhexidine. U.S. Pat. No. 5,772,640 reported on polymeric medical articles comprising the anti-infective agents, chlorhexidine and triclosan. U.S. Pat. No. 5,362,754 disclosed preventing glycocalyx formation on a catheter by coating with EDTA and/or minocycline, preventing bacterial and fungal infections. U.S. Pat. No. 6,258,797 disclosed combating infection or sepsis in catheter and port systems by using an anti-microbial locking solution of taurolidine or taurultam.

U.S. Pat. No. 6,166,007 disclosed anti-microbial locks comprising taurinamide derivatives and carboxylic acids and/or salts thereof for preventing infection and blood coagulation in or near a medical prosthetic device after the device has been inserted in a patient. EP 1,040,841 described prevention of thrombosis formation and/or bacterial growth on a liquid-contacting surface of a delivery system by contacting the surface with a thrombosis-preventing liquid having anti-coagulant agent, taurolidine, and/or taurultam. EP 882,461 disclosed a medical device having both physiological and anti-microbial activity comprising a base material, a crosslinked coating film formed on a surface of the base material, and each of a physiologically active substance and an anti-microbial substance bonded to the coating film.

Boorgu et al., *ASAIO J.*, 46 (6): 767-770 (Nov. 2000) published on an adjunctive antibiotic/anticoagulant lock therapy in the treatment of bacteremia associated with the use of a subcutaneously implanted hemodialysis access device. Attached to the device are two catheters that are implanted into the superior vena cava or right atrium. An antibiotic/anticoagulant lock therapy entailed the instillation of both an antibiotic and an anticoagulant into the device. See also Schwartz et al., *Journal of Clinical Oncology.*, 8(9):1591-1597 (1990) and Kamal et al., *JAMA*, 265(18):2364-2368 (1991).

Wiernikowski et al., *Am J. Pediatr Hematol Oncol.* 13(2): 137-140 (1991) disclosed that bacteriostatic saline flush solutions prevented catheter infections compared to normal saline. Vercaigne et al., *Pharmacotherapy*, 20: 394-9 (2000) evaluated heparin plus antibiotics as a locking solution to prevent infection. Patel et al., *Thromb Hemost*, 82: 1205-6 (1999) disclosed successful use of low-dose r-hirudin for recurrent dialysis catheter thrombosis in a patient with heparin-induced thrombocytopenia. Darouiche et al., *Nutrition*, 13(4)(suppl): 26S-29S (1997) reported that the prevention of vascular catheter-related infection can be achieved using antimicrobial agents involving the application of topical disinfectants such as chlorhexidine, use of silver-impregnated subcutaneous cuffs (for short-term CVCs), flushing of catheters with a combination of anti-microbial and anti-thrombotic agents, and coating of catheters with either antiseptic (chlorhexidine and silver sulfadiazine) or anti-microbial agents (minocycline and rifampin).

Antibacterial lock solutions have been used to clean out catheters. For example, U.S. Pat. No. 6,174,537 disclosed a catheter flush solution. See also Sodermann et al. *Blood Purif.*, 19: 251-254 (2001) on DIALOCK™ and CLS; the TUBEX™ Heparin Lock Flush Solution (Wyeth-Ayerst); and Henrickson et al., *J. Clin Oncol.*, 18: 1269-1278 (2000) on prevention of CVC-related infections and thrombotic events using vancomycin/cipro-floxacin/heparin flush solution.

Soft-cuffed, implantable CVCs such as the QUINTON PERMCATH™ CVC (Quinton Instrument Co., Seattle, Wash.) are increasingly used in patients with end-stage renal disease as a means of permanent access. Their major limitations, besides infection, are thrombosis and inadequate blood flow. To prevent those complications, heparin is conventionally used for priming the QUINTON PERMCATH™ CVC between dialysis sessions. Schenk et al., *Amer. J. Kidney Diseases*, 35: 130-136 (Jan. 2000) showed that recombinant tissue-plasminogen activator (rt-PA) was superior to heparin for priming the QUINTON PERMCATH™ CVC between hemodialysis sessions. However, Schenk et al. utilized 2 mg of alteplase plus SWFI (sterile water for injection, USP), which does not prevent growth of bacteria.

Central venous access device (CVAD) occlusions or blockages due to formation of a blood clot (thrombus) within or at the tip of the CVAD catheter are a common problem that can block the administration of therapies to patients. Estimates suggest that 25% of CVADs become occluded, with thrombosis as the most common etiology (Haire et al., *Thromb. Haemost*, 72: 543-547 (1994); Rubin, *J. Clin. Oncol.*, 1: 572-573 (1983); Lokich et al., *J. Clin. Oncol.*, 3: 710-717 (1985)). In 1994, Haire et al., supra, performed a double-blind, prospective, randomized trial of urokinase versus alteplase (t-PA) in dysfunctional catheters proven radiographically to be occluded by thrombus. Catheters were treated with 2 mg of alteplase or 10,000 U of urokinase that was allowed to dwell in the device for 2 hours. After up to two treatments, alteplase restored function in more catheters than urokinase (89% versus 59% (p=0.013)).

On Sep. 4, 2001 the U.S. Food and Drug Administration (FDA) approved the thrombolytic agent CATHFLO™ ACTIVASE® (alteplase) t-PA, for the restoration of function to CVADs, as assessed by the ability to withdraw blood. CATHFLO™ ACTIVASE® t-PA is available in a 2-mg, single-patient-use vial, is the only marketed thrombolytic available for this indication, and offers medical professionals a viable treatment option for a CVAD complication that can hinder patient care. One vial of CATHFLO™ t-PA contains 2.2 mg of alteplase, 77 mg of L-arginine, 0.2 mg of POLYSORBATE 80™ emulsifier, and phosphoric acid to adjust the pH to approximately 7.3.

T-PA has been bonded to other materials than vascular catheters. See, for example, Zhou et al., *J. Control Release*, 55: 281-295 (1998); Greco et al., *Ann Vasc. Surg*, 9: 140-145 (1995) and Woodhouse et al., *Biomaterials*, 17: 75-77 (1996).

U.S. Pat. No. 5,688,516 disclosed use of selected combinations of a chelating agent, anticoagulant, or anti-thrombotic agent, with a non-glycopeptide anti-microbial agent, such as the tetracycline antibiotics, to coat a medical device and to inhibit catheter infection. Preferred combinations include minocycline or another non-glycopeptide anti-microbial agent together with EDTA, EGTA, DTPA, TTH, heparin, and/or hirudin in a pharmaceutically acceptable diluent. U.S. Pat. No. 6,187,768 similarly disclosed use of an anti-microbial agent and an anticoagulant, an anti-thrombotic agent, or a chelating agent to maintain the patency of indwelling medical devices such as catheters and for preventing infections caused by bacterial growth in catheters.

Notwithstanding the above-described contributions to the art, a need continues to exist for a non-toxic method for removal of fibrin-bound blood clots from catheters, especially indwelling medical devices. There is a further need for the prevention and the removal of fibrin from such devices, as certain bacteria have binding sites that favor sticking to fibrin, in particular.

SUMMARY OF THE INVENTION

The present invention discloses solutions unique in their ability to meet the above needs, which are not based on anti-coagulation, anti-thrombotic, or chelating activities and do not involve the use of antibiotics, for which mammals can develop resistance. The present invention solves the needs set forth herein by using a plasminogen activator in conjunction with a disinfectant used as a preservative, mainly an organic alcohol that serves in this capacity. The resulting composition not only has fibrinolytic activity, but also prevents pathogen growth, especially in clotted catheters, and has passed USP standards.

The invention is as claimed. Specifically, in one aspect the present invention provides a composition useful for removal of fibrin-bound blood clots from a catheter comprising water, a fibrinolytically effective amount of a plasminogen activator, and a preservatively effective amount of a bacteriostatic organic alcohol, wherein the composition does not comprise a chelating agent.

In another aspect the invention provides a multi-compartment package comprising a compartment comprising a fibrinolytically effective amount of a plasminogen activator, a compartment comprising water containing a preservatively effective amount of a bacteriostatic organic alcohol, wherein neither compartment comprises a chelating agent, and instructions for mixing the contents of both compartments and for using the resulting mixture to remove fibrin-bound blood clots from a catheter that contains such blood clots.

In yet another aspect, the invention provides a multi-compartment package comprising a compartment comprising from about 0.1 to 10 mg/mL of native-sequence t-PA or tenecteplase and a compartment comprising water containing about 0.5 to 1.2% (v/v) of benzyl alcohol, isopropanol, or ethanol, wherein neither compartment comprises a chelating agent, and instructions for mixing the contents of both compartments and for using the resulting mixture to remove fibrin-bound blood clots from a catheter that contains such blood clots.

The preferred amount of benzyl alcohol, a preferred alcohol herein, is about 0.8-1.1%. This range and the broader range of about 0.5 to 1.2% are enough to inhibit microbe growth but preserve stability and function of the plasminogen activator. An advantage of these alcohols is that they do not lead to antibiotic resistance.

In a still further embodiment, the invention provides a method for removing fibrin-bound blood clots from a catheter that contains such blood clots comprising contacting the catheter with the above composition for at least about 5 days.

In a yet further embodiment, the invention provides a catheter coated with the above-identified composition.

BRIEF DESCRIPTION OF THE DRAWINGS

FIG. 1 shows reduced SEC chromatograms of reconstituted rt-PA (1 mg/mL with BWFI, BNS, and SWFI) after 14 days of storage at 37° C. in glass vials.

DETAILED DESCRIPTION OF THE PREFERRED EMBODIMENTS

Definitions

As used herein, "catheter" refers to a medical device generally constructed of plastic polymers such as, for example, polyurethane, silicone, or other such polymers for the purpose of delivering medical therapy and withdrawing blood. Such catheters represent a wide variety of indwelling medical devices such as a urinary catheter, a vascular catheter such as a CVC or a peripheral intravenous catheter, an arterial catheter, a tracheal catheter, a Swan-Ganz catheter, a hemodialysis catheter, an umbilical catheter, a percutaneous non-tunneled silicone catheter, a cuffed tunneled central venous catheter, and a subcutaneous central venous port, and the like.

"Vascular catheter" is used herein to describe a catheter involving the vascular system and includes peripheral catheters and CVCs, long-term cuffed devices, short-term, non-cuffed devices, and implantable ports. CVCs, which are the same as central venous access devices (CVADs), include peripherally inserted central catheters (PICC lines), external cuffed devices, non-cuffed catheters, non-tunneled and subcutaneously tunneled catheters, hemodialysis (HD) catheters, and ports.

The preferred catheters herein are an indwelling catheter such as a CVC, preferably a cuffed tunneled CVC, a peripheral intravenous catheter, an arterial catheter, a Swan-Ganz catheter, a hemodialysis catheter, an umbilical catheter, a percutaneous non-tunneled silicone catheter, or a subcutaneous central venous port. Also preferred is a urinary catheter or a peritoneal catheter. Additionally preferred are an intravenous catheter, one that is fabricated from a biomedical polyurethane or silicone, or a vascular catheter.

As used herein, "preparation" or "composition" refers to a composition, solution, formulation, or the like that is an admixture of the ingredients set forth.

As used herein, the terms "contact," "contacting," and the like mean exposure to a reagent, by any means, such as coating, incubating, etc.

The terms "coat", "coated," etc., as used herein, refer to dipping, soaking, treating, and/or impregnating a catheter with the composition herein.

As used herein, "bacteriostatic organic alcohol" means an organic alcohol that is a disinfectant used as a preservative, and not classified as an antibiotic or in a class of antibiotic. Disinfectants, which are chemicals that inhibit or kill microorganisms, are defined in *Basic and Clinical Pharmacology*, 8th edition (2001), Section VII. Chemotherapeutic Drugs. Chapter 50. Miscellaneous Antimicrobial Agents—Disinfectants, Antiseptics, and Sterilants. Preservatives are chemicals used to prevent microbial spoilage of preparations. Disinfectants are used as preservatives to prevent the overgrowth of bacteria and fungi in pharmaceutical preparations. They must be effective in preventing growth of microorganisms likely to contaminate them, and must have sufficient solubility and stability to remain active, as per *Ellenhorn's Medical Toxicology* 2nd Ed (1997), Section IV. Chemicals. Chapter 57. Antiseptics and Disinfectants. Examples of such organic alcohol preservatives include ethanol, isopropanol, and benzyl alcohol, which are preferred herein, with benzyl alcohol being most preferred. Benzyl alcohol, which is hydrophobic, can disrupt cell walls and membranes of microorganisms, denature proteins, and inactivate enzymes.

"Bacteriostatic water for injection" or "BWFI" refers to a mixture of water and varying amounts of benzyl alcohol and water with no other ingredients as defined by the United States Pharmacopeia (USP).

As used herein, "sterile water for injection" or "SWFI" is sterile water alone without any other ingredient.

As used herein, "normal saline" or "NS" is a mixture of water with an appropriate amount (such as 0.9% (w/v)) of sodium chloride, with no other ingredients.

As used herein, "bacteriostatic normal saline" or "BNS" refers to sterile water with an appropriate amount (such as 0.9% (w/v)) of sodium chloride and with an appropriate amount (i.e., one that is preservatively effective) of a bacteriostatic organic alcohol such as benzyl alcohol without any other ingredient.

As used herein, the term "plasminogen activator" means a fibrinolytic single- or double-chain plasminogen activator, including urinary plasminogen activator in native or variant form, tissue plasminogen activator in a native form such as ACTIVASE®) alteplase t-PA or in variant form such as r-PA (reteplase; RETAVASE®; Centocor, Inc.) and tenecteplase (a t-PA variant designated T103N, N117Q, K296A, H297A, R298A,R299A available as TNKASE™ brand from Genentech, Inc. and described, for example, in U.S. Pat. No. 5,612, 029), as well as urokinase (e.g., ABBOKINASE®; Abbott), which may be a naturally occurring native molecule or a variant of urokinase that has the function of a fibrinolytic in dissolving clots in the blood and preventing and removing fibrin. Preferably, the plasminogen activator is native-sequence t-PA, a fibrinolytic t-PA variant, native-sequence urokinase, or a fibrinolytic urokinase variant. More preferably, the plasminogen activator is native-sequence t-PA, a fibrinolytic t-PA variant, or native-sequence urokinase. Still more preferably, the plasminogen activator is native-sequence t-PA or a fibrinolytic t-PA variant. Still more preferably, the t-PA variant is tenecteplase or reteplase. Most preferably the plasminogen activator is native-sequence t-PA or tenecteplase.

As used herein, "chelating agent" means an agent used for chelating, such as ethylenediaminetetraacetic acid (EDTA), DMSA, deferoxamine, dimercaprol, zinc citrate, TRICITRASOL™ (a citrate calcium chelator), a combination of bismuth and citrate, penicillamine, succimer, or etidronate. Ethylene glycol-bis-(beta-aminoethyl ether)-N,N,N',N'-tetraacetic acid (EGTA) and diethylenetriamine pentaacetic acid (DTPA) and salts thereof are other known chelating agents, as well as edetate calcium disodium, triethylene tetramine dihydrochloride, and those that chelate divalent metal cations such as Ca, Mg, Mn, Fe and Zn.

Modes for Carrying Out the Invention

The present invention provides a composition useful for removal of fibrin-bound blood clots from a catheter comprising water, a fibrinolytically effective amount of a plasminogen activator, and a preservatively effective amount of a bacteriostatic organic alcohol. The composition does not contain a chelating agent.

The water preferably contains the bacteriostatic organic alcohol to begin with. There are generally four types of diluents that are used to dilute or reconstitute drugs: BWFI, SWFI, BNS, and NS. The present invention includes only those that are bacteriostatic, i.e., BWFI and BNS. Preferably, the water containing the alcohol is bacteriostatic water for injection or is bacteriostatic normal saline.

The pH of the composition herein must be appropriate for biological use. Typically, the composition or solution of the present invention will have a pH in the range of from about 3 to 7, preferably from about 3.5 to 6.5 and, most preferably from about 4.5 to 6.5. The composition will normally be at a physiological pH. If necessary, the pH can be adjusted by additional acid or base, such as a mineral acid, for example, hydrochloric acid, or, preferably, one that will not cause acidosis, such as, for example, acetic, malic, or lactic acid. Other methods for adjusting the pH, familiar to those of skill in the art, can also be employed.

A test for whether the amount of plasminogen activator in the composition is fibrinolytically effective can be done, for example, by in vitro clot lysis assays, such as those described in the Examples provided herein.

The preservatively effective amount of alcohol can be determined, for example, by the anti-microbial effectiveness test set forth in the Examples below. Preferably the amount of plasminogen activator is from about 0.1 to 10 mg/mL and the preservatively effective amount of organic alcohol is preferably from about 0.5 to 1.2% (v/v). More preferably, the fibrinolytically effective amount of plasminogen activator is from about 0.3 to 5 mg/mL, still more preferably from about 0.5 to 4 mg/mL, and most preferably from about 1 to 3 mg/mL. The more preferred amount of organic alcohol is from about 0.8 to 1.1% (v/v).

The composition of the invention is preferably exposed to conditions that substantially render any microorganisms therein non-viable and packaged in a sealed vessel, such as a syringe, a septum-closed vial, or an ampoule that is substantially resistant to the passage of microorganisms. Preferably, the sealed vessel contains an aliquot of the flush solution that is sufficient to perform one catheter flush procedure. For particular applications, a bulk vessel may be preferred that contains a sufficient amount of the solution to dispense multiple aliquots for individual catheter flush procedures.

A method for flushing an intravenous catheter includes providing an admixed solution as set forth above and contacting the catheter with such solution for at least about two hours. The method includes filling a fluid-handling device, preferably a syringe, with an aliquot of the solution sufficient to perform a catheter flush procedure. The preferred amount for the flush procedure is generally about one to three milliliters. The practitioner then attaches the syringe to the target intravascular catheter that requires flushing and administers the solution into the catheter, thereby completing the flush procedure.

The method herein may be used to remove preexisting blood clots at virtually any tunneled or untunneled catheter. As part of a catheter maintenance or flushing regimen, the catheter most preferably is to be flushed with the composition herein, for example, once a week, once every 4 days, once every 2 days, once a day (about every 24 hours), twice a day, every four hours or as needed according to patient needs, as would be known to the skilled practitioner. The catheter-flushing regimen may simply constitute once every time that the catheter is changed. In a preferred aspect of the method, the catheter is to be flushed more frequently at four-hour intervals with the compositions herein.

Although the method of this invention applies to introducing the composition into catheters that are already in place, those skilled in the art will understand that contacting or coating the catheter outside the body with the composition can prevent the deposition of fibrin on such surface after its implantation and reduce sites for bacterial growth. Thus, the surfaces of catheters, such as hemodialysis catheters, can be pretreated by the composition herein. The catheter can be treated with a composition initially and then, after insertion, subjected to repeated periodic flushing.

Particular exemplary catheters that may be prepared and coated with the compositions of the present invention are provided in the above list. In the coating method the plasminogen activator, water, and alcohol are present in amounts such that their combination, in the treated article, has effective fibrinolytic and preservative activity. In a specific embodiment, the catheter is a polyurethane or silicone catheter (or one made from similar polymers) that has been treated with (i.e., dipped or soaked in) a treatment solution as set forth above. The surface of the catheter of interest is then exposed to the composition for a period of time sufficient to allow the formation of a film or coating of the composition on the exposed surface of the device. As a liquid, the composition would be allowed to dry on the surface of the device so as to form a film.

The amount of the composition herein injected into a catheter will be sufficient to fill it. Such devices, when they are hemodialysis catheters, typically have internal volumes in the range of from about 0.1 to 10 mL. Such quantities will, of course, vary with the length and diameter of the tubing of the device, which, inter alla, can be a function of the size of the individual patient.

If fibrin-bound blood clots are being removed from a catheter the catheter may be contacted with the solution herein for at least about 5 days, preferably about 6 to 15 days.

The present invention in still another aspect provides a kit or package. In one embodiment, the kit or package comprises a container means, such as a compartmentalized syringe, that comprises at least two separate compartment means. One compartment or container means comprises a fibrinolytically effective amount of a plasminogen activator such as t-PA, and the second container means or compartment comprises water containing a preservatively effective amount of a bacteriostatic organic alcohol. As with the composition, neither compartment comprises a chelating agent. The package also contains instructions for mixing the contents of both compartments and for using the resulting mixture to remove fibrin-bound blood clots from a catheter that contains such blood clots. The t-PA may be a lyophilized powder that in dry powder form is then reconstituted when mixed with the water to provide a solution suitable for use. The kit may additionally include a container that is a carrier means adapted to receive the contents of the two compartments. The package herein may be a kit, wherein each compartment is a separate container such as a vial or ampoule, or the package may be a multi-compartment syringe.

Various features and aspects of the present invention are illustrated further in the examples that follow. While these examples are presented to show one skilled in the art how to operate within the scope of the invention, they are not intended in any way to serve as a limitation upon the scope of the invention. The disclosure of all citations herein is expressly incorporated herein by reference.

EXAMPLE 1 (COMPARATIVE)

Summary

Testing was performed as described below to evaluate the anti-microbial properties of 2 mg/mL of ACTIVASE® t-PA when reconstituted in SWFI. This sample did not meet the requirement of the USP anti-microbial effectiveness test.

USP Anti-Microbial Effectiveness Test

This test is used to evaluate the efficacy of a preservative in a formulation or to assess the intrinsic anti-microbial activity of an active ingredient. It is described in USP 24, "Microbiological Tests/(51) Antimicrobial Effectiveness Testing, pages 1809-1811.

A. Materials and Major Equipment

1. The challenge organisms used were *Escherichia coli*, ATCC 8739, *Pseudomonas aeruginosa*, ATCC 9027, *Staphylococcus aureus*, ATCC 6538, *Candida albicans*, ATCC 10231, and *Aspergillus niger*, ATCC 16404.

2. Media, supplies, and major equipment were:
   Trypticase soy agar (TSA)
   Sabouraud dextrose agar (SDA)
   Phosphate buffered saline (PBS), sterile, pH 7.2±0.2
   Sterile 50-mL conical tubes
   Sterile swabs and serological pipettes
   Spectrophotometer
   Colony counter, Quebec or equivalent
   Incubators at 2-8° C., 22.5±2.5° C., and 32.5±2.5° C.

B. Procedure

1. Preparation of inoculum:

Each organism suspension was prepared to achieve an approximate concentration of $1 \times 10^8$ colony-forming units (CFU)/mL. Each of the five tubes containing 10 mL of sample was inoculated with 0.05 mL of its corresponding challenge organism, resulting in an initial concentration from between $1 \times 10^5$ CFU/mL and $1 \times 10^6$ CFU/mL of the test preparation. The initial population of viable organisms in each test preparation was calculated based on the concentration of the organisms in each of the standardized inocula by the Pour Plate Method. This method is a common microbiological technique to count the number of organisms in a test sample. The test sample is diluted with sterile saline and pipetted onto a sterile Petri dish. Then melted agar (the nutrient media) is poured into the Petri dish and mixed with the sample and incubated at a standardized temperature and time. This method yields colonies that form throughout the agar—not just on the surface.

Approximately 10 mL of sample was poled into a tube left uninoculated to serve as a Negative Control. At T=day 7, day 14, and day 28, the population of each organism in the inoculated samples and in the Negative Control was determined by the Pour Plate Method, the validated plate count method. Incubation conditions for the Pour Plate Method are shown in Table 1.

2. Validation of the Pour Plate Method:

The sample was serially diluted to obtain $10^{-1}$ and $10^{-2}$ dilutions. A 1-mL portion of each sample dilution was added to each of 5 Petri plates. For each sample dilution, a 0.1-mL aliquot containing approximately $1 \times 10^3$ CFU/mL of each challenge organism was added to its corresponding Petri plate. In parallel, the same inoculum volume of each organism was aliquoted into each of two plates without the sample dilutions for count confirmation. A 15-20 mL portion of molten agar held at approximately 45° C. was added to each plate and swirled gently to mix the contents. The plates were allowed to solidify and incubated as indicated in Table 1.

3. Preparation of sample 10 mL of sample was delivered into each of five vials. Each vial was labeled separately with "EC", "PA", "SA", "CA", and "AN", so one vial was labeled for each organism to be tested. Ten mL of sample was delivered into one vial labeled negative control. Alternatively, for the delivering and labeling steps above, 20 mL of sample was delivered into each vial.

4. Bioburden determination

Using the negative control, the bioburden of the sample was determined by the Pour Plate Method. The media and incubation conditions were used as set forth in Table 1.

5. Inoculation of sample 0.05 mL of each of the organism suspensions was inoculated at 1×10⁸ CFU/mL into the corresponding sample vial containing 10 mL of sample. The volume of the suspension inoculum used was 0.5% of the volume of the sample. The mixture was vortexed thoroughly. The final concentration of the test preparation was approximately $5.0 \times 10^5$ CFU/mL. Alternatively, if a 20-mL sample volume was used in each vial, for the inoculation step above 0.1 mL of each of the challenge suspensions was delivered.

6. Initial concentration count confirmation

The plate count of each standardized inoculum was determined ($1.0 \times 10^8$ CFU/mL) by the Pour Plate Method. The media and incubation conditions used are set forth in Table 1. The plate counts were performed in duplicate to obtain the average plate count of each standardized inoculum. The initial concentration of each challenge organism in the test preparation was calculated using the following equation:

$$S \times \frac{I}{P}$$

where

S=average organism concentration of standardized suspension ($1.0 \times 10^8$ CFU/mL)

I=inoculum volume (0.05 mL)

P=volume of test preparation (10 mL)

7. Sample storage and test intervals

The inoculated containers and the negative control were incubated at 22.5±2.5° C. protected from light. Each container was sampled at specified time points in Table 2. The plate count of the inoculated samples and the negative control was performed by the Pour Plate Method. The plate count was performed in duplicate. Media and incubation conditions were used as set forth in Table 1.

TABLE 1

Incubation Conditions for Pour Plate Method

| Organism | Suitable Medium | Incubation Temperature (° C.) | Incubation Time (days) |
|---|---|---|---|
| E. coli ATCC 8739 | TSA | 32.5 ± 2.5 | 3-5 |
| P. aeruginosa ATCC 9027 | TSA | 32.5 ± 2.5 | 3-5 |
| S. aureus ATCC 6538 | TSA | 32.5 ± 2.5 | 3-5 |
| C. albicans ATCC 10231 | SDA | 22.5 ± 2.5 | 3-5 |
| A. niger ATCC 16404 | SDA | 22.5 ± 2.5 | 3-7 |

TABLE 2

Plating Time Points for Parenterals

| | 0 hr | 6 hr | 24 hr | 7 d | 14 d | 28 d |
|---|---|---|---|---|---|---|
| USP (bacteria, yeast, and mold) | NA | NA | NA | R | R | R |
| EP (bacteria) | R | R | R | R | R | R |
| EP (yeast and mold) | R | NA | NA | R | R | R |

NA = not applicable
R = required

C. Acceptance Criteria

1. For a valid challenge study, the concentration of challenge organisms in each test preparation was between $1 \times 10^5$ CFU/mL and $1 \times 10^6$ CFU/mL. There was no detectable bioburden in the sample used in the validated plate count method.

2. For a valid plate count method, the average count of the recovered inocula at each dilution level must be greater than or equal to 50% of the average count for the corresponding control. If the average count of the recovered inocula at a dilution. If the average count is less than 50%, all counts at that dilution are considered invalid.

D. Interpretation

1. USP

For bacteria, there should be not less than a 1.0 log reduction from the initial calculated count at 7 days, not less than 3.0 $\log_{10}$ reduction from the initial count at 14 days, and no increase from the 14-day count at 28 days.

For yeast and mold, there should be no increase from the initial calculated count at 7, 14, and 28 days. "No increase" is defined as not more than 0.5 $\log_{10}$ unit higher than the previous value measured.

2. EP

The criteria for evaluation of anti-microbial activity for parental preparations are in Table 3 in terms of the log reduction in the number of viable microorganisms against the value obtained for the inoculum.

TABLE 3

EP Criteria for Evaluation of Anti-microbial Activity for Parenterals

| | | Log Reduction | | | | |
|---|---|---|---|---|---|---|
| | Criteria* | 6 h | 24 h | 7 d | 14 d | 28 d |
| Bacteria | A | 2 | 3 | — | — | NR |
| Bacteria | B | — | 1 | 3 | — | NI |
| Fungi | A | — | — | 2 | — | NI |
| Fungi | B | — | — | — | 1 | NI |

NR = No recovery.
NI = No increase. "No increase" is defined as not more than 0.3 $\log_{10}$ unit higher than the previous value measured.
*The A criteria expresses the recommended efficacy to be achieved. In justified cases where the A criteria cannot be attained, for example, for reasons of an increased risk of adverse reactions, the B criteria must be satisfied.

Test with ACTIVASE® t-PA and SWFI

A. Materials, Equipment, and Procedures

The sample was 2 mg/mL of ACTIVASE® alteplase t-PA in a vial with SWFI containing no benzyl alcohol.

The challenge organisms and all media, supplies, and major equipment were those set forth in the test above. The procedure used was the same as that described in the test above, and the incubation conditions were as in Table 1. The acceptance criteria and interpretation were the same as in the test above.

Results

The calculated initial concentration of challenge organisms in each test preparation was between $1\times10^5$ CFU/mL and $1\times10^6$ CFU/mL (Table 4).

There was no detectable bioburden in the sample using the Pour Plate Method (Table 5).

The plate count method was validated using the Pour Plate Method. The average recovered inoculum at the $10^{-1}$ dilution of the sample was greater than or equal to 50% of the average of the corresponding control (Table 6).

For *P. aeruginosa* and *S. aureus*, there was a greater than or equal to 1.3 $\log_{10}$ reduction from the calculated initial concentration at day 7, a less than 3.0 $\log_{10}$ reduction at day 14 and a greater than or equal to 3.6 $\log_{10}$ reduction at day 28 (Tables 7 and 8). For *E. coli*, there was a less than 1.0 $\log_{10}$ reduction from the calculated initial concentration at day 7 and a less than 3.0 $\log_{10}$ reduction at day 14 and day 28 (Tables 7 and 8).

For yeast and mold, there was a greater than or equal to 0.6 $\log_{10}$ reduction from the calculated initial concentration at day 7, a greater than or equal to 1.0 $\log_{10}$ reduction at day 14, and a greater than or equal to 1.6 $\log_{10}$ reduction at day 28 (Tables 7 and 8).

TABLE 4

Calculated Initial Concentration of Challenge Organisms

| Challenge organism | Suspension concentration (CFU/mL) | Calculated Initial Concentration (CFU/mL) |
|---|---|---|
| P. aeruginosa | $7.7 \times 10^7$ | $3.9 \times 10^5$ |
| E. coli | $1.2 \times 10^8$ | $6.0 \times 10^5$ |
| S. aureus | $3.9 \times 10^7$ | $2.0 \times 10^5$ |
| C. albicans | $7.2 \times 10^7$ | $3.6 \times 10^5$ |
| A. niger | $1.2 \times 10^8$ | $6.0 \times 10^5$ |

TABLE 5

Bioburden of Sample by the Pour Plate Method

| Media | CFU Recovered from $10^{-1}$ Sample Dilution | Bioburden (CFU/mL) |
|---|---|---|
| TSA | 0 | <10 |
| SDA | 0 | <10 |

TABLE 6

Average Recovered Inoculum by the Pour Plate Method

| Challenge Organism | Average CFU Inoculated | Average CFU Recovered from $10^{-1}$ dilution | Average Percent Recovery (%) |
|---|---|---|---|
| P. aeruginosa | 65 | 48 | 74 |
| E. coli | 93 | 110 | 118 |
| S. aureus | 43 | 55 | 129 |
| C. albicans | 84 | 74 | 88 |
| A. niger | 59 | 46 | 79 |

TABLE 7

Microbial Population over 28 Days

| Challenge Organisms | Initial Calculated Count (CFU/mL) | 7 days (CFU/mL) | 14 days (CFU/mL) | 28 days (CFU/mL) |
|---|---|---|---|---|
| P. aeruginosa | $3.9 \times 10^5$ | $6.3 \times 10^3$ | $1.1 \times 10^4$ | 50 |
| E. coli | $6.0 \times 10^5$ | $1.2 \times 10^5$ | $1.3 \times 10^6$ | $7.2 \times 10^5$ |
| S. aureus | $2.0 \times 10^5$ | $9.1 \times 10^3$ | $7.4 \times 10^2$ | 55 |
| C. albicans | $3.6 \times 10^5$ | <100 | <10 | <10 |
| A. niger | $6.0 \times 10^5$ | $1.5 \times 10^5$ | $5.8 \times 10^4$ | $1.4 \times 10^4$ |
| Negative Control | <10 | <10 | <10 | <10 |

TABLE 8

Log Reduction of Microbial Population over 28 Days

| Challenge Organisms | Log Reduction | | |
|---|---|---|---|
| | 7 days | 14 days | 28 days |
| P. aeruginosa | 1.8 | 1.5 | 3.9 |
| E. coli | 0.7 | −0.3 | −0.1 |
| S. aureus | 1.3 | 2.4 | 3.6 |
| C. albicans | >3.6 | >4.6 | >4.6 |
| A. niger | 0.6 | 1.0 | 1.6 |

Discussion

In the bacterial anti-microbial effectiveness test, this sample did not meet the USP requirements. There was a <1.0 $\log_{10}$ reduction of the calculated initial concentration at day 7 for *E. coli*. At day 14, the log reduction of all three bacterial test organisms was a <3.0 $\log_{10}$. For yeast and mold, there was no increase from the initial calculated count at 7, 14, and 28 days.

EXAMPLE 2

Summary

Testing was performed as disclosed above for anti-microbial effectiveness to evaluate the efficacy of 0.8% benzyl alcohol as a preservative in 2 mg/mL of ACTIVASE® t-PA against the USP requirements. This sample met the requirements of the USP anti-microbial effectiveness test.

Materials, Equipment, and Procedures

The sample was ACTIVASE® t-PA (2 mg/mL) in a vial with 0.8% benzyl alcohol. Specifically, the diluent was sterile water plus the appropriate amount of benzyl alcohol for a final concentration of 0.8%.

The challenge organisms were those described in Example 1.

Media, supplies, and major equipment were the same as noted in Example 1.

The procedure used was the same as that described in Example 1 and the incubation conditions were as in Table 1. The acceptance criteria and interpretation were the same as in Example 1.

Results

The results were the same as in Table 4 and Table 5 for calculated initial concentration of challenge organisms in each test preparation (between $1\times10^5$ and $1\times10^6$ CFU/mL) and for bioburden in the sample using the Pour Plate Method (no detectable bioburden). The plate count method was validated using the Pour Plate Method. The average recovered inoculum at the $10^{-1}$ dilution of the sample was greater than or equal to 50% of the average of the corresponding control (Table 9). For bacteria, there was a >3.3 $\log_{10}$ reduction from the calculated initial concentration at day 7, and a >4.3 $\log_{10}$ reduction at day 14 and day 28 (Tables 10 and 11). For yeast and mold, there was a greater than or equal to 3.1 $\log_{10}$ reduction from the calculated initial concentration at day 7, and a greater than 4.6 $\log_{10}$ reduction at day 14 and day 28 (Tables 10 and 11).

TABLE 9

Average Recovered Inoculum by the Pour Plate Method

| Challenge organism | Average CFU inoculated | Average CFU recovered from $10^{-1}$ dilution | Average percent recovery |
|---|---|---|---|
| P. aeruginosa | 65 | 60 | 92 |
| E. coli | 93 | 99 | 106 |
| S. aureus | 43 | 55 | 129 |
| C. albicans | 84 | 82 | 97 |
| A. niger | 59 | 50 | 85 |

TABLE 10

Microbial Population over 28 days

| Challenge organisms | Initial Calculated Count (CFU/mL) | 7 days (CFU/mL) | 14 days (CFU/mL) | 28 days (CFU/mL) |
|---|---|---|---|---|
| P. aeruginosa | $3.9 \times 10^5$ | <100 | <10 | <10 |
| E. coli | $6.0 \times 10^5$ | <100 | <10 | <10 |
| S. aureus | $2.0 \times 10^5$ | <100 | <10 | <10 |
| C. albicans | $3.6 \times 10^5$ | <100 | <10 | <10 |
| A. niger | $6.0 \times 10^5$ | 500 | <10 | <10 |
| Negative control | <10 | <10 | <10 | <10 |

TABLE 11

Log Reduction of Microbial Population over 28 Days

| Challenge organisms | Log Reduction | | |
|---|---|---|---|
| | 7 days | 14 days | 28 days |
| P. aeruginosa | >3.6 | >4.6 | >4.6 |
| E. coli | >3.8 | >4.8 | >4.8 |
| S. aureus | >3.3 | >4.3 | >4.3 |
| C. albicans | >3.6 | >4.6 | >4.6 |
| A. niger | 3.1 | >4.8 | >4.8 |

Conclusion

This sample met the requirements of the USP anti-microbial effectiveness test.

EXAMPLE 3

Summary

Testing was performed as disclosed above for anti-microbial effectiveness to evaluate the efficacy of 0.9% benzyl alcohol as a preservative in 2 mg/mL of ACTIVASE® t-PA against the USP requirements. This sample met the requirements of the USP anti-microbial effectiveness test.

Materials, Equipment, and Procedures

The sample was ACTIVASE® t-PA (2 mg/mL) in a vial with 0.9% benzyl alcohol. Specifically, the diluent was sterile water plus the appropriate amount of benzyl alcohol for a final concentration of 0.9%.

The challenge organisms were those described in Example 1.

Media, supplies, and major equipment were the same as noted in Example 1.

The procedure used was the same as that described in Example 1 and the incubation conditions were as in Table 1. The acceptance criteria and interpretation were the same as in Example 1.

Results

The results were the same as in Table 4 and Table 5 for calculated initial concentration of challenge organisms in each test preparation (between $1 \times 10^5$ and $1 \times 10^6$ CFU/mL) and for bioburden in the sample using the Pour Plate Method (no detectable bioburden). The plate count method was validated using the Pour Plate Method. The average recovered inoculum at the $10^{-1}$ dilution of the sample was greater than or equal to 50% of the average of the corresponding control (Table 12). For bacteria, there was a >3.3 $\log_{10}$ reduction from the calculated initial concentration at day 7, and a >4.3 $\log_{10}$ reduction at day 14 and day 28 (Tables 13 and 14). For yeast and mold, there was a greater than or equal to 3.6 $\log_{10}$ reduction from the calculated initial concentration at day 7, and a greater than 4.6 $\log_{10}$ reduction at day 14 and day 28 (Tables 13 and 14).

TABLE 12

Average Recovered Inoculum by the Pour Plate Method

| Challenge organism | Average CFU inoculated | Average CFU recovered from $10^{-1}$ dilution | Average percent recovery |
|---|---|---|---|
| P. aeruginosa | 65 | 58 | 89 |
| E. coli | 93 | 91 | 97 |
| S. aureus | 43 | 43 | 100 |
| C. albicans | 84 | 76 | 90 |
| A. niger | 59 | 38 | 65 |

TABLE 13

Microbial Population over 28 days

| Challenge organisms | Initial Calculated Count (CFU/mL) | 7 days (CFU/mL) | 14 days (CFU/mL) | 28 days (CFU/mL) |
|---|---|---|---|---|
| P. aeruginosa | $3.9 \times 10^5$ | <100 | <10 | <10 |
| E. coli | $6.0 \times 10^5$ | <100 | <10 | <10 |
| S. aureus | $2.0 \times 10^5$ | <100 | <10 | <10 |
| C. albicans | $3.6 \times 10^5$ | <100 | <10 | <10 |
| A. niger | $6.0 \times 10^5$ | <100 | <10 | <10 |
| Negative control | <10 | <10 | <10 | <10 |

TABLE 14

Log Reduction of Microbial Population over 28 Days

| Challenge organisms | Log Reduction | | |
|---|---|---|---|
| | 7 days | 14 days | 28 days |
| P. aeruginosa | >3.6 | >4.6 | >4.6 |
| E. coli | >3.8 | >4.8 | >4.8 |
| S. aureus | >3.3 | >4.3 | >4.3 |
| C. albicans | >3.6 | >4.6 | >4.6 |
| A. niger | >3.8 | >4.8 | >4.8 |

Conclusion

This sample met the requirements of the USP anti-microbial effectiveness test.

In one suggested priming application, a solution of CATH-FLO™ ACTIVASE® (alteplase) 2.2. mg lyophilized powder reconstituted with 2.2 mL of 0.9% benzyl alcohol in sterile bacteriostatic water for injection (1 mg/mL concentration) can be placed inside a vascular catheter in equal volume to the catheter lumen priming volume. The solution can then be aspirated from the catheter and discarded prior to using the catheter for medical purposes.

EXAMPLE 4

Summary

Testing was performed as disclosed above for anti-microbial effectiveness to evaluate the efficacy of 1.0% benzyl alcohol as a preservative in 2 mg/mL of ACTIVASE® t-PA against the USP requirements. This sample met the requirements of the USP anti-microbial effectiveness test.

Materials, Equipment, and Procedures

The sample was ACTIVASE® t-PA (2 mg/mL) in a vial with 1.0% benzyl alcohol. Specifically, the diluent was sterile water plus the appropriate amount of benzyl alcohol for a final concentration of 1.0%.

The challenge organisms were those described in Example 1.

Media, supplies, and major equipment were the same as noted in Example 1.

The procedure used was the same as that described in Example 1 and the incubation conditions were as in Table 1. The acceptance criteria and interpretation were the same as in Example 1.

Results

The results were the same as in Table 4 and Table 5 for calculated initial concentration of challenge organisms in each test preparation (between $1\times10^5$ and $1\times10^6$ CFU/mL) and for bioburden in the sample using the Pour Plate Method (no detectable bioburden). The plate count method was validated using the Pour Plate Method. The average recovered inoculum at the $10^{-1}$ dilution of the sample was greater than or equal to 50% of the average of the corresponding control (Table 15). For bacteria, there was a >3.3 $\log_{10}$ reduction from the calculated initial concentration at day 7, and a >4.3 $\log_{10}$ reduction at day 14 and day 28 (Tables 16 and 17). For yeast and mold, there was a greater than or equal to 4.1 $\log_{10}$ reduction from the calculated initial concentration at day 7, and a greater than 4.6 $\log_{10}$ reduction at day 14 (Tables 16 and 17).

TABLE 15

Average Recovered Inoculum by the Pour Plate Method

| Challenge organism | Average CFU inoculated | Average CFU recovered from $10^{-1}$ dilution | Average percent recovery |
|---|---|---|---|
| P. aeruginosa | 65 | 64 | 98 |
| E. coli | 93 | 94 | 101 |
| S. aureus | 43 | 43 | 101 |
| C. albicans | 84 | 79 | 94 |
| A. niger | 59 | 48 | 81 |

TABLE 16

Microbial Population over 28 days

| Challenge organisms | Initial Calculated Count (CFU/mL) | 7 days (CFU/mL) | 14 days (CFU/mL) | 28 days (CFU/mL) |
|---|---|---|---|---|
| P. aeruginosa | $3.9 \times 10^5$ | <100 | <10 | <10 |
| E. coli | $6.0 \times 10^5$ | <100 | <10 | <10 |
| S. aureus | $2.0 \times 10^5$ | <100 | <10 | <10 |
| C. albicans | $3.6 \times 10^5$ | <100 | <10 | <10 |
| A. niger | $6.0 \times 10^5$ | 50 | <10 | <10 |
| Negative control | <10 | <10 | <10 | <10 |

TABLE 17

Log Reduction of Microbial Population over 28 Days

| Challenge organisms | Log Reduction | | |
|---|---|---|---|
| | 7 days | 14 days | 28 days |
| P. aeruginosa | >3.6 | >4.6 | >4.6 |
| E. coli | >3.8 | >4.8 | >4.8 |
| S. aureus | >3.3 | >4.3 | >4.3 |
| C. albicans | >3.6 | >4.6 | >4.6 |
| A. niger | 4.1 | >4.8 | >4.8 |

Conclusion

This sample met the requirements of the USP anti-microbial effectiveness test.

EXAMPLE 5

Summary

Testing was performed as disclosed above for anti-microbial effectiveness to evaluate the efficacy of 1.1% benzyl alcohol as a preservative in 2 mg/mL of ACTIVASE® t-PA against the USP requirements. This sample met the requirements of the USP anti-microbial effectiveness test.

Materials, Equipment, and Procedures

The sample was ACTIVASE® t-PA (2 mg/mL) in a vial with 1.1% benzyl alcohol. Specifically, the diluent was sterile water plus the appropriate amount of benzyl alcohol for a final concentration of 1.1%.

The challenge organisms were those described in Example 1.

Media, supplies, and major equipment were the same as noted in Example 1.

The procedure used was the same as that described in Example 1 and the incubation conditions were as in Table 1. The acceptance criteria and interpretation were the same as in Example 1.

Results

The results were the same as in Table 4 and Table 5 for calculated initial concentration of challenge organisms in each test preparation (between $1\times10^5$ and $1\times10^6$ CFU/mL) and for bioburden in the sample using the Pour Plate Method (no detectable bioburden). The plate count method was validated using the Pour Plate Method. The average recovered inoculum at the $10^{-1}$ dilution of the sample was greater than or equal to 50% of the average of the corresponding control (Table 18).

For bacteria, there was a >3.3 $\log_{10}$ reduction from the calculated initial concentration at day 7, and a >4.3 $\log_{10}$ reduction at day 14 and day 28 (Tables 19 and 20). For yeast and mold, there was a greater than or equal to 3.6 $\log_{10}$ reduction from the calculated initial concentration at day 7, and a greater than 4.6 $\log_{10}$ reduction at day 14 and day 28 (Tables 19 and 20).

TABLE 18

Average Recovered Inoculum by the Pour Plate Method

| Challenge organism | Average CFU inoculated | Average CFU recovered from $10^{-1}$ dilution | Average percent recovery |
|---|---|---|---|
| P. aeruginosa | 65 | 61 | 94 |
| E. coli | 93 | 118 | 127 |
| S. aureus | 43 | 54 | 127 |
| C. albicans | 84 | 77 | 91 |
| A. niger | 59 | 47 | 79 |

TABLE 19

Microbial Population over 28 days

| Challenge organisms | Initial Calculated Count (CFU/mL) | 7 days (CFU/mL) | 14 days (CFU/mL) | 28 days (CFU/mL) |
|---|---|---|---|---|
| P. aeruginosa | $3.9 \times 10^5$ | <100 | <10 | <10 |
| E. coli | $6.0 \times 10^5$ | <100 | <10 | <10 |
| S. aureus | $2.0 \times 10^5$ | <100 | <10 | <10 |
| C. albicans | $3.6 \times 10^5$ | <100 | <10 | <10 |
| A. niger | $6.0 \times 10^5$ | <100 | <10 | <10 |
| Negative control | <10 | <10 | <10 | <10 |

TABLE 20

Log Reduction of Microbial Population over 28 Days

| Challenge organisms | Log Reduction | | |
|---|---|---|---|
| | 7 days | 14 days | 28 days |
| P. aeruginosa | >3.6 | >4.6 | >4.6 |
| E. coli | >3.8 | >4.8 | >4.8 |
| S. aureus | >3.3 | >4.3 | >4.3 |
| C. albicans | >3.6 | >4.6 | >4.6 |
| A. niger | >3.8 | >4.8 | >4.8 |

Conclusion

This sample met the requirements of the USP anti-microbial effectiveness test.

EXAMPLE 6

Summary

Alteplase (2 mg/vial rt-PA) was reconstituted to 1 mg/mL with BWFI, BNS, and SWFI. The stability of the protein after reconstitution in glass vials was monitored at 37° C. for 2 weeks. After 14 days of storage at 37° C., all the reconstituted solutions appeared as clear and colorless. The protein concentrations (1.1±0.02 mg/mL) and pH (7.2±0.03) remained unchanged. The percent monomer by native SEC showed a gradual decrease by 1-3% and 4-5% after one and two weeks at 37° C., respectively. A decrease in percent single-chain and clot lysis activity (in vitro) was observed after one week at 37° C. However, the percent single-chain and clot-lysis activity (in vitro) was drastically reduced after 14 days at 37° C. More proteolytic clippings of the molecule were observed for the protein solution reconstituted with SWFI than with BWFI or BNS. Therefore, alteplase (2 mg/vial rt-PA) reconstituted with BWFI, BNS, or SWFI to 1 mg/mL was relatively stable at 37° C. for one week.

Materials and Methods

A. Materials

Alteplase (2-mg vial rt-PA)

BWFI, USP, 20 mL (Abbott)

Bacteriostatic 09% sodium chloride (w/v) (BNS) injection, USP, 20 mL (Abbott)

SWFI, USP, 20 mL (Abbott)

B. Methods

Alteplase (2 mg/vial rt-PA) was reconstituted to 1 mg/mL with BWFI, BNS, or SWFI (in duplicate). The reconstituted protein solutions were stored at 37° C. The stability of the reconstituted protein solutions after storage for 3 hours, 7 days, and 14 days at 37° C. was assessed by the assays listed below.

For particle counts by HIAC/ROYCO, a separate experiment was performed. Alteplase (2-mg rt-PA) was reconstituted with BWFI, BNS, or SWFI (in duplicate) to 1 mg/mL. Four vials per group for each time point were combined together in a single vial (original 5-mL glass vial). The particle counts (3×1 mL sampling, discarding the first run) were taken at T=0, 3 hours, 7 days, and 14 days after storage at 37° C.

C. Assays (1) Color and Clarity. Each sample in a glass vial was examined under a light box equipped with a black and white background. The color and clarity of the sample were recorded accordingly.

(2) HIAC/ROYCO. Four vials of the reconstituted protein solution were combined for the measurement. The procedure for particulate matter analysis for small-volume parenterals was employed with the modification that a sample volume of 1 mL was tested using a 1-mL syringe instead of a 5-mL volume using a 10-mL syringe. Particle counts in the size range of $\geqq10$ and $\geqq25$ pm were recorded.

(3) pH. The pH of selected aliquots was determined using a RADIOMETER PHM 93™ pH meter equipped with a combination pH electrode (Microelectrodes, Inc.). The pH meter was standardized with pH 4.01 and 7.00 standard buffers (Mallinckrodt, Inc.). 20 μL of the aliquots were transferred to a 0.5-mL Eppendorf tube for measurement.

(4) Concentration by UV. The protein concentration was determined by UV absorption at 280 nm. A UV/VIS diode array spectrophotometer (HP8253A) was employed with a 1-cm path-length quartz cuvette for measurement. The samples were diluted 10 to 12.5 fold with formulation buffer. The measurement was blanked against the proper reference and an UV scan from 240 to 400 nm was taken. The protein concentration was calculated as follows:

Conc., mg/mL=(A280−A320)/1.9, where 1.9 is the absorptivity (mL/mg-cm) of rt-PA at 280 nm.

(5) % Monomer by native SEC. A TSK 3000SWXL™ (ToSoHaas, 300×7.5-mm i.d., 5-μm) column was employed on a HP1090™ liquid chromatography column (LC) equipped with a Diode-Array detector. The mobile phase was 0.2 M arginine, 0.12 M ammonium sulfate, 10% isopropanol, pH 7.3. The flow rate was 1 mL/min. The samples (50 μg of rt-PA equivalent) were injected in singlet and the chromatograms collected with detection at 280 nm. The percent monomer is calculated as follows:

% monomer=(monomer peak area/total peak area attributed to protein)×100

(6) % Single chain by reduced SEC. A TSK 3000SWXL™ (ToSoHaas, 300×7.5-mm i.d., 5-μm) column was employed on a HP1090™ LC equipped with a Diode-Array detector. The mobile phase was 0.2 M sodium phosphate, 0.1% SDS, pH 6.8. The flow rate was 1 mL/min. The samples (12.5 μg of rt-PA equivalent) were incubated with 20 mM DTT (final concentration) at 37° C. for 3-5 minutes and injected in singlicate. The chromatograms were monitored with detection at 214 nm. The percent single chain (SC) is calculated as follows:

% SC=(first main peak area/sum of the first and second main peak area)×100.

(7) Purified clot lysis activity for rt-PA. The potency of the protein was assessed by the purified clot lysis assay described in Example 7 below. Samples were diluted to assay range (200-1000 ng/mL) in two concentrations with diluent. Dilutions were performed the day before the assay and diluted samples were stored at 2-8° C. until analysis the next day. rt-PA reference material was diluted similarly as an internal reference.

Results

The results of the study are shown in Tables 21 and 22. After 14 days of storage at 37° C., all the reconstituted solutions appeared as clear and colorless. The protein concentrations (1.1±0.02 mg/mL) and pH (7.2±0.03) remained unchanged. Table 21 shows the particle counts by HIAC/ROYCO of the reconstituted alteplase (2 mg/vial rt-PA, n=1) at 1 mg/mL with BWFI, BNS, and SWFI after storage at 37° C. The table indicates an increase in particle counts (≧10 and 25 μm) for all protein solutions after reconstitution compared to the diluent alone. However, all the results are well within the USP limits for Small Volume Injection (SVI, see Table 23). There appeared to be a decrease in particle counts for the reconstituted drug product stored over time at 37° C. The particle counts result also showed a lower number of counts for protein solutions reconstituted with BWFI and BNS than with SWFI.

All the reconstituted solutions had 94-95% monomer remaining after 14 days at 37° C. (Table 22). Both the % single chain and clot lysis activity (in vitro) tests showed a decrease after one week at 37° C. The % single chain is higher for the protein solutions reconstituted with BWFI or BNS than with SWFI. Without being limited to any one theory, this may be the result of the preservative inhibiting the proteolytic activity. After two weeks at 37° C., the percent single chain for the protein solutions reconstituted with SWFI dropped to equal to or less than 50%, which is below the stability specification (≧55%) for the single chain in rt-PA.

In addition to the conversion of one chain to two chains, the reduction SEC chromatograms of the reconstituted protein solutions after two weeks at 37° C. revealed clippings/fragments of the molecule, suggesting increased proteolytic cleavage at elevated temperature with time (see FIG. 1). FIG. 1 clearly shows that in addition to the clippings or fragments, more conversion of one-chain to two-chain rt-PA was observed in the reconstituted rt-PA with SWFI than with BWFI or BNS after storage at 37° C. for 14 days.

The clot-lysis activity (in vitro) indicated that all the reconstituted alteplase solutions (1 mg/mL) retained greater than or equal to 100% potency after three hours at 37° C. (Table 23). All samples were colorless or clear. The activity began to drop after one week of storage at 37° C., but about 90% of the activity (relative to initial, T=0) still remained. There was a drastic reduction in activity after two weeks at 37° C., with only 44-65% activity remaining.

TABLE 21

Particle Counts by HIAC/ROYCO of Reconstituted Alteplase (1 mg/mL, 2 mg/vial rt-PA) Stored at 37° C. for 3 Hours, 7 Days, and 14 Days

| | HIAC/ROYCO | | | |
|---|---|---|---|---|
| | ≧10 μm/mL | ≧10 μm/vial | ≧25 μm/mL | ≧25 μm/vial |
| T = 0: | | | | |
| BWFI | 89 | 196 | 5.5 | 12 |
| rt-PA/BWFI | 725.5 | 1596 | 7 | 15 |
| T = 0: | | | | |
| BNS | 50 | 110 | 7 | 15 |
| rt-PA/BNS | 474.5 | 1044 | 8.5 | 19 |
| T = 3 h, 37° C. | | | | |
| BWFI | 1 | 2 | 0 | 0 |
| rt-PA/BWFI | 474 | 948 | 3.5 | 8 |
| T = 3 h, 37° C. | | | | |
| BNS | 10.5 | 23 | 0 | 0 |
| rt-PA/BNS | 200 | 440 | 1 | 2 |
| T = 0: | | | | |
| SWFI | 10.5 | 23 | 0 | 0 |
| rt-PA/SWFI | 603 | 1327 | 10.5 | 23 |
| T = 0: | | | | |
| BWFI | 2.5 | 6 | 0 | 0 |
| rt-PA/BWFI | 877.5 | 1931 | 18.5 | 41 |
| T = 0: | | | | |
| BNS | 2 | 4 | 0 | 0 |
| rt-PA/BNS | 225 | 495 | 2.5 | 6 |
| T = 7 d, 37° C.: | | | | |
| SWFI | 13.5 | 30 | 0 | 0 |
| rt-PA/SWFI | 302.5 | 666 | 0 | 0 |
| T = 7 d, 37° C. | | | | |
| BWFI | 2 | 4 | 0 | 0 |
| rt-PA/BWFI | 132.5 | 292 | 1 | 2 |
| T = 7 d, 37° C. | | | | |
| BNS | 2 | 4 | 0 | 0 |
| rt-PA/BNS | 32.5 | 72 | 0.5 | 1 |

TABLE 21-continued

Particle Counts by HIAC/ROYCO of Reconstituted Alteplase (1 mg/mL, 2 mg/vial rt-PA) Stored at 37° C. for 3 Hours, 7 Days, and 14 Days

|  | HIAC/ROYCO | | | |
|---|---|---|---|---|
|  | ≧10 μm/mL | ≧10 μm/vial | ≧25 μm/mL | ≧25 μm/vial |
| T = 0: | | | | |
| SWFI | 6.5 | 14 | 0 | 0 |
| rt-PA/SWFI | 796.5 | 1752 | 6 | 13 |
| T = 0: | | | | |
| BWFI | 4.5 | 10 | 0 | 0 |
| rt-PA/BWFI | 564 | 1241 | 13.5 | 30 |
| T = 0: | | | | |
| BNS | 1 | 2 | 0 | 0 |
| rt-PA/BNS | 587 | 1291 | 4 | 9 |
| T = 14 d, 37° C.: | | | | |
| SWFI | 4.5 | 10 | 0 | 0 |
| rt-PA/SWFI | 491 | 1080 | 2.5 | 6 |
| T = 14 d, 37° C.: | | | | |
| BWFI | 1.3 | 3 | 0 | 0 |
| rt-PA/BWFI | 56.3 | 124 | 3 | 7 |
| T = 14 d, 37° C.: | | | | |
| BNS | 0.5 | 1 | 0 | 0 |
| rt-PA/BNS | 55 | 121 | 0 | 0 |

TABLE 22

Stability of Reconstituted Alteplase (2 mg/vial rt-PA) to 1 mg/mL with BWFI, BNS, and SWFI in Glass Vials at 37° C.

|  |  | pH | Conc. (by SEC) mg/mL | Native SEC (% monomer) | Reduced SEC (% SC) | Clot lysis (mg/mL) | ($\times 10^3$ IU/mg) | Relative % activity* |
|---|---|---|---|---|---|---|---|---|
| T = 0: | | | | | | | | |
| rtPA/BWFI | A | 7.23 | 1.11 | 98.7 | 85.5 | 0.97 ± 0.02 | 5.07 | 100 |
|  | B | 7.24 | 1.11 | 98.6 | 85.5 | 1.00 ± 0.01 | 5.23 | 100 |
| T = 0: | | | | | | | | |
| rtPA/BNS | A | 7.18 | 1.11 | 98.4 | 85.5 | 1.03 ± 0.02 | 5.38 | 100 |
|  | B | 7.19 | 1.09 | 98.3 | 85.5 | 0.99 ± 0.05 | 5.27 | 100 |
| T = 0: | | | | | | | | |
| rtPA/SWFI | A | 7.26 | 1.10 | 98.3 | 85.5 | 1.07 ± 0.02 | 5.64 | 100 |
|  | B | 7.25 | 1.10 | 98.2 | 85.4 | 1.04 ± 0.04 | 5.48 | 100 |
| T = 3 h, 37° C.: | | | | | | | | |
| rtPA/BWFI | A | 7.24 | 1.12 | 98.3 | 85.2 | 1.08 ± 0.005 | 5.59 | 110 |
|  | B | 7.25 | 1.08 | 98.2 | 98.3 | 1.01 ± 0.035 | 5.42 | 104 |
| T = 3 h, 37° C.: | | | | | | | | |
| rtPA/BNS | A | 7.18 | 1.11 | 98.0 | 85.3 | 1.07 ± 0.01 | 5.59 | 104 |
|  | B | 7.20 | 1.10 | 97.9 | 85.3 | 1.04 ± 0.015 | 5.48 | 104 |
| T = 3 h, 37° C.: | | | | | | | | |
| rtPA/SWFI | A | 7.25 | 1.11 | 98.2 | 85.2 | 1.04 ± 0.04 | 5.43 | 96 |
|  | B | 7.25 | 1.10 | 98.1 | 85.2 | 1.11 ± 0.035 | 5.85 | 107 |
| T = 7 d, 37° C.: | | | | | | | | |
| rtPA/BWFI | A | 7.25 | 1.12 | 95.9 | 72.8 | 0.86 ± 0.03 | 4.45 | 88 |
|  | B | 7.26 | 1.11 | 96.2 | 73.0 | 0.92 ± 0.025 | 4.81 | 92 |
| T = 7 d, 37° C.: | | | | | | | | |
| rtPA/BNS | A | 7.20 | 1.10 | 96.9 | 75.1 | 0.91 ± 0.045 | 4.80 | 89 |
|  | B | 7.20 | 1.07 | 97.0 | 74.9 | 0.89 ± 0.005 | 4.82 | 91 |
| T = 7 d, 37° C.: | | | | | | | | |
| rtPA/SWFI | A | 7.28 | 1.11 | 97.5 | 68.7 | 1.00 ± 0.03 | 5.23 | 93 |
|  | B | 7.27 | 1.12 | 97.2 | 67.6 | 0.94 ± 0.01 | 4.87 | 89 |

TABLE 22-continued

Stability of Reconstituted Alteplase (2 mg/vial rt-PA) to 1 mg/mL with BWFI, BNS, and SWFI in Glass Vials at 37° C.

| | | pH | Conc. (by SEC) mg/mL | Native SEC (% monomer) | Reduced SEC (% SC) | Clot lysis (mg/mL) | (×10³ IU/mg) | Relative % activity* |
|---|---|---|---|---|---|---|---|---|
| T = 14 d 37° C.: | | | | | | | | |
| rtPA/B WFI | A | 7.26 | 1.10 | 94.5 | 58.0 | 0.56 ± 0.02 | 2.95 | 58 |
| | B | 7.27 | 1.09 | 93.8 | 58.4 | 0.57 ± 0.03 | 3.03 | 58 |
| T = 14 d 37° C.: | | | | | | | | |
| rtPA/B NS | A | 7.22 | 1.11 | 94.0 | 62.2 | 0.62 ± 0.015 | 3.24 | 60 |
| | B | 7.22 | 1.10 | 93.9 | 62.1 | 0.62 ± 0 | 3.27 | 62 |
| T = 14 d 37° C.: | | | | | | | | |
| rtPA/ SWFI | A | 7.31 | 1.16 | 94.0 | 49.2 | 0.73 ± 0 | 3.65 | 65 |
| | B | 7.29 | 1.16 | 93.9 | 49.0 | 0.48 ± 0.01 | 2.40 | 44 |

*% Activity (IU/mg) relative to initial (T = 0).

TABLE 23

| Limits for Particulate Matter in Injections | | |
|---|---|---|
| Small-volume Injections, SVI (per container basis): | >10 μm | >25 μm |
| Light obscuration | 6000 | 600 |
| Microscopic | 25 | 3 |

Conclusion

Alteplase (2 mg/vial rt-PA) reconstituted with BWFI, BNS, or SWFI to 1 mg/mL was relatively stable at 37° C. for one week in a glass vial. It is believed that the BNS solution would be anti-microbial, since it is the benzyl alcohol that is the active ingredient. Stability testing using BNS was positive, i.e., alteplase was stable and functional.

EXAMPLE 7

Summary

T-PA diluted down to 0.01 mg/mL in normal saline was found to be lytically active in a clot lysis effectiveness test. In such test, thrombin and fibrinogen are mixed together to produce fibrin; plasminogen and rt-PA are mixed together to produce plasmin; and together the fibrin and plasmin lyse the clot. The test measures the effectiveness of t-PA to act with plasminogen to form plasmin and thus lyse the clot.

Materials and Methods

A. Materials:

Alteplase (2 mg/vial rt-PA) was diluted to a concentration of 0.01, 0.025, 0.05, and 0.1 mg/mL final protein concentration in 0.9% NaCl (Normal Saline, NS)-containing IV bags (Baxter and/or Abbott, 250 mL). Specifically, rt-PA, protein bulk, was diluted to 1 mg/mL (50-mg vial formulation equivalent, 0.004% TWEEN 80™ surfactant) with filtered MILLI-Q™ water, or a 100-mg vial rt-PA was reconstituted to 1 mg/mL (0.008-0.011% TWEEN 80™ surfactant) with Sterile Water for Injection, USP (SWFI) using a 60-cc BD syringe and an 18 G needle directly inserted into the rubber septum of the vial at the center of the cake. The vial was gently mixed by slow inversions or rolling action until the cake was totally dissolved. IV diluent (0.9% NaCl, NS) was withdrawn and replaced with the same amount of the reconstituted or diluted 1 mg/mL rt-PA as follows:

| Final Conc. (mg/mL) | Vol. (mL) removed from a 250-mL IV bag* (Then replaced with same vol. of 1 mg/mL rt-PA) |
|---|---|
| 0.05 | 12.5 (30-cc BD syringe and 18G needle) |
| 0.024 | 6 (10-cc BD syringe and 22G needle) |
| 0.01 | 2.5 (3- or 5-cc BD syringe and 22G needle) |

*Overfill of bag was not accounted for.

After dilution into the IV bags (n=2 for each concentration), the bags were gently mixed by inversion (about 20-24 times). A 10-mL aliquot was withdrawn from the inlet port of the IV bag using a 10-cc BD syringe and 22 G needle. An aliquot (t=0) was dispensed directly into a 20-cc Type I clear glass vial for visual inspection. Similarly, placebo equivalents at 0.025 and 0.05 mg/mL were also physically examined.

B. Assays:

1. Visual Inspection

Each aliquot was examined under a light box equipped with a black and white background. The aliquots were compared to an equal volume of SWFI or filtered MILLI-Q™ water in a same-size glass vial that served as a control. The color and clarity of the aliquots were recorded accordingly.

2. Purified Clot Lysis Test (Microcentrifugal Analyzer (Test 1) and Plate Reader (Test 2)):

The potency of the alteplase t-PA protein was assessed by the purified clot lysis assay described below. Samples were diluted to assay range (200-1000 ng/mL) in three or two concentrations with diluent. Dilutions were performed the day before the assay and diluted samples were stored at 2-8° C. until analysis the next day. Rt-PA reference material was diluted similarly as an internal reference.

a. Equipment:

IL MONARCH Microcentrifugal Analyzer model no. 761™ was used, consisting of an analyzer assembly with fluorescence and light-scattering capability and built-in computer, and a loader assembly.

b. Reagents:

1% (v/v) POLYSORBATE 80™ emulsifier(JT Baker).

Assay buffer: 0.06 M sodium phosphate (0.0114 F $NaH_2PO_4.H_2O$, 0.0486 F $Na_2HPO_4$) with 0.02% (w/v) $NaN_3$ and 0.01% (v/v) POLYSORBATE 80™ emulsifier, pH 7.4±0.1.

Human thrombin (30-40 units/mL) (Calbiochem) kept in an unopened vial frozen at or below −60° C. until ready for use.

Plasminogen kept frozen at or below −60° C. until use.

Biocell fibrinogen prepared as follows: Fibrinogen and clot lysis buffer were brought to room temperature. A total of 7 mL of clot lysis buffer was added to the vial. The vial was capped and parafilmed. The vial was placed on its side in a dish or taped to an orbital shaker. The speed was set between 4 and 5. The vial was shaken for up to one hour, while it was checked to see how well the cake was dissolving. When the cake was completely dissolved, the solution was transferred to a 50-mL Falcon tube. The vial was rinsed at least three times with clot lysis buffer, and the rinses were transferred into a Falcon tube to catch any residual globules or particles. The solution was brought to a final volume of 30 mL using the markings on the tube. The tube was parafilmed and put on the shaker for 15-30 minutes. All protein was solubilized after shaking. The solution was set on wet ice for at least 2-3 hours and gently shaken periodically. Using WHATMAN™ No. 1 paper, the solution was filtered by decanting the solution away from the precipitate. The filtered solution was kept on ice.

Reference material (standard ACTIVASE® t-PA). All solutions containing t-PA were kept in polystyrene or polypropylene containers.

c. Preparation of Standards:

Starting with the reference material, a 10-µg/mL standard stock solution was prepared. The dilution was recorded on assay data sheets. The remaining standards were prepared according to the following dilution scheme. All standards were kept on ice and the expiration of the standard curve was 12 hours from the time of preparation.

| Standard | rt-PA Source | Assay Buffer |
| --- | --- | --- |
| 200 ng/mL | 200 µL of standard stock | 9.8 mL |
| 400 ng/mL | 400 µL of standard stock | 9.6 mL |
| 600 ng/mL | 600 µL of standard stock | 9.4 mL |
| 800 ng/mL | 800 µL of standard stock | 9.2 mL |
| 1000 ng/mL | 1000 µL of standard stock | 9.0 mL |

The preparation of standard stock solution and of remaining standards was repeated to prepare two standard curves.

d. Preparation of Sample:

i. Initial preparation

If the sample was a final vial of lyophilized material, it was reconstituted volumetrically to 1 mg/mL with water for injection (WFI). If the sample was a sterile bulk material, it was diluted to 1 mg/mL with WFI.

ii. Sample stock preparation

Using a micropipet, 100 µL of the 1.0-mg/mL rt-PA sample was pipetted into a 15-mL polystyrene tube. A total of 9.90 mL of assay buffer was added to the tube using a 10-mL graduated polystyrene pipette or volumetric pipette plus micropipette. This solution was designated as the sample stock solution.

iii. Working sample preparation

Using a micropipet, 600 µL of the sample stock solution was pipetted into a 15-mL polystyrene tube. 9.40 mL of assay buffer was added to the tube using a 10-mL graduated polystyrene pipette, or volumetric pipette plus micropipette. This was the sample solution to load into the sample cups. The diluted samples were kept on ice.

iv. The sample stock preparation and working sample preparation steps were repeated to prepare two sample dilutions.

v. Positive assay control preparation

The control was prepared by reconstituting a sample of rt-PA to 1 mg/mL, pipetting 0.5-mL aliquots into Eppendorf tubes, and freezing at −60° C. A new tube was thawed on each day the assay was run. The control was diluted using 100 µL of sample in the same manner as the sample. The diluted control samples were kept on ice.

e. Procedure for MONARCH 2000™ Analyzer (Assay 1):

The assay works as follows: Reagents are substances added to a solution of another substance to participate in a chemical reaction. In this case, contents of boat 1 will react with contents of boat 2 to form a standardized clot. Thrombin (boat 2), when mixed with plasminogen and fibrinogen (boat 1), causes the conversion of fibrinogen to fibrin and forms a standardized in vitro clot consisting of plasminogen and fibrin. A test sample of t-PA is then exposed to the clot. T-PA causes the conversion of plasminogen to plasmin, and plasmin then breaks apart the fibrin strands. As the clot breaks apart, there is a change in the absorbance (light) characteristics. The absorbance is plotted versus time.

The pipette tips of the analyzer were checked to ensure they were properly aligned, and the water reservoir was checked to be sure that it was full. Syringes were debubbled if necessary and the wash cycle was performed.

The analyzer parameters were as shown in Table 24.

TABLE 24

| Analyzer Parameters | |
| --- | --- |
| Identification Parameters | |
| Test code | 24 |
| Test name | General absorbance |
| Test mnemonic | GNABS |
| Optical mode | Absorbance |
| Loading Parameters | |
| Loading type | Load (Crit.) incubate analyze |
| Reagent blank | on |
| Reference type | diluent |
| Sample volume | 20 µL |
| Sample diluent | 0 µL |
| Reagent diluent | 0 µL |
| 1st reagent | 200 µL |
| 2nd reagent | 20 µL |
| 1st Reagent bar code | T1 |
| 2nd Reagent bar code | T2 |
| Data Acquisition Parameters | |
| Analysis type | Mix Run |
| Temperature | 37° C. |
| Incubate time | 5 min. |
| Delay time | 280 sec* |
| Interval time | 5 sec* |
| No. of data points | 90* |

TABLE 24-continued

Analyzer Parameters

| Filter 1 | 340 nm |
|---|---|
| Filter 2 | 340 nm |
| Monochromator 1 | 340 nm |
| Monochromator 2 | 340 nm |

*These items should be adjusted accordingly to ensure full data acquisition.

Reagent boat 1 was prepared by adding 200 μL of reconstituted plasminogen to 10.0 mL of filtered fibrinogen. This was mixed gently and put into reagent boat 1. The reagent boat 1 was placed into the first position of the analyzer reagent table.

Reagent boat 2 was prepared by adding the 33 units/mL thrombin solution described above to reagent boat 2. Reagent boat 2 was placed into position 2 in the analyzer.

The 0.25-mL sample cups were placed in the sample ring. Using disposable transfer pipettes or a PIPETMAN™ pipette, the sample cups were filled with standard, control, and samples as indicated in Table 25, Suggested Loading Scheme. If fewer than two samples were being run, the loading was done as indicated and the assay buffer or water was pipetted into any intervening empty sample cups.

TABLE 25

Suggested Loading Scheme

| Sample ID | Cup No. | Cuvette No. |
|---|---|---|
| 200 ng/mL Standard (I) | 1 | 3 |
| 400 ng/mL Standard (I) | 2 | 4 |
| 600 ng/mL Standard (I) | 3 | 5 |
| 800 ng/mL Standard (I) | 4 | 6 |
| 1000 ng/mL Standard (I) | 5 | 7 |
| assay control rep 1 | 6 | 8 |
| 200 ng/mL Standard (II) | 7 | 9 |
| sample 1 dil 1 rep 1 | 8 | 10 |
| sample 1 dil 2 rep 1 | 9 | 11 |
| sample 2 dil 1 rep 1 | 10 | 12 |
| sample 2 dil 2 rep 1 | 11 | 13 |
| assay control rep 2 | 12 | 14 |
| 400 ng/mL Standard (II) | 13 | 15 |
| sample 1 dil 1 rep 2 | 14 | 16 |
| sample 1 dil 2 rep 2 | 15 | 17 |
| sample 2 dil 1 rep 2 | 16 | 18 |
| sample 2 dil 2 rep 2 | 17 | 19 |
| assay control rep 3 | 18 | 20 |
| 600 ng/mL Standard (II) | 19 | 21 |
| sample 1 dil 1 rep 3 | 20 | 22 |
| sample 1 dil 2 rep 3 | 21 | 23 |
| sample 2 dil 1 rep 3 | 22 | 24 |
| sample 2 dil 2 rep 3 | 23 | 25 |
| assay control rep 4 | 24 | 26 |
| 800 ng/mL Standard (II) | 25 | 27 |
| sample 1 dil 1 rep 4 | 26 | 28 |
| sample 1 dil 2 rep 4 | 27 | 29 |
| sample 2 dil 1 rep 4 | 28 | 30 |
| sample 2 dil 2 rep 4 | 29 | 31 |
| assay control rep 5 | 30 | 32 |
| 1000 ng/mL Standard (II) | 31 | 33 |
| sample 1 dil 1 rep 5 | 32 | 34 |
| sample 1 dil 2 rep 5 | 33 | 35 |
| sample 2 dil 1 rep 5 | 34 | 36 |
| sample 2 dil 2 rep 5 | 35 | 37 |

The "Special request" button was pressed on the MONARCH™ Analyzer. The sample cup information was entered. The "Accept" button was pressed twice. After the MONARCH™ Analyzer finished pipetting, the reagent boats were removed and placed on ice. The sample ring was removed and placed in the refrigerator at 2-8° C.

i. Endpoint Determination:

The endpoint (lysis time) may be determined by a computer program or manually. For automatic calculation by computer, the endpoint is the time required to lyse the clot, which is determined automatically. For manual endpoint determination, the endpoint is defined as the first time point below 0.03 absorbance units where the change is less than 0.003 abs unit. Specifically, for manual determination, the endpoint was determined from the absorbance time data. The first absorbance point less than 0.0300 was located. The endpoint was determined as the time of the first absorbance value less than 0.0300 if the change in absorbance between the current absorbance and the subsequent absorbance was less than 0.0030. If the delta absorbance was greater than 0.0030, one moved to the next absorbance reading and determined the delta absorbance. The endpoint was the first absorbance value of the pair (initial and subsequent absorbance value) where the delta absorbance was less than 0.0030.

ii. Calculations:

The mean lysis time for each standard curve point was calculated. The standard concentrations (ng/mL) and the mean endpoint times (which are in seconds) were converted to log values. A standard curve of log concentration (x-axis) versus log time (y-axis) was prepared.

Using the slope and intercept values obtained from the linear regression analysis, the log concentration for each sample was calculated from the log lysis time (endpoint). The antilog of the obtained log concentration was taken and multiplied by the dilution factor (e.g., 1667) to obtain units/mL.

$$*(\text{units/mL}) = \text{antilog}\left[\frac{[\log \text{lysis time} - y\text{-intercept}]}{[\text{slope}]}\right] \times \frac{1 \text{ mg}}{1,000,000 \text{ ng}} \times (\text{sample dilution}) \times (1 \text{ unit/mg}).$$

The system suitability of the standard curve was evaluated using the system suitability test. For a determination to be valid under this test, the correlation coefficient for the standards must be between −0.997 and −1.000, and the control within ±10% of its accepted value. If system suitability was not met, the standard curve could be redefined by performing the linear regression analysis using no fewer than four contiguous points (i.e., the first or last standard may be omitted).

The results were reported as units/vial, units/mg, units/mL, IU/vial, IU/mg, or IU/mL, as required. For the control, all five replicates were averaged. System suitability was assessed as described above. For final vial samples, all five replicates per sample dilution were averaged. The average result was reported from the two sample dilutions. This was reported in units/vial, where units/vial=average units/mL×mL/vial. For bulk samples, the five replicates per sample dilution were averaged. The average result was reported from the two sample dilutions. The report was in units/mg where:

$$*\text{specific activity(units/mg)} = \frac{\text{units of activity mL}}{\text{mg of protein/mL}}$$

*Units/mL or units/mg may be converted to international units (IU)/mL or IU/mg by multiplication by the appropriate international unit conversion factor.

For COA and stability testing, the testing of the sample was repeated using one rotor per each of three days. The average of the results from the three days was reported. The assay may be repeated based on the results of the in-house control and/or based on determinate or indeterminate error. The final results may be reported as an average of multiple tests.

f. Procedure for the Plate Reader Assay 2:

The plate reader was turned on and the temperature of the thermostat was set to 25° C. The lamp was allowed to warm up for at least half an hour. Thrombin was added in an amount of 20 μL to each well. Thrombin may be added from a reagent reservoir or from an interim plate using the multichannel pipette. 20 μL per well of diluted standards (in duplicate) was added to wells B2-B6 and C2-C6. 20 μL per well of the control was added to wells D2-G2, and 20 μL of the samples was added into the remaining wells in quadruplicate in a vertical format to a maximum of nine samples per plate. Wells in rows B-G not containing standards, controls, or samples should contain 20 μL of assay diluent. The rt-PA samples may be added individually with a single channel pipette or from an interim plate using the multichannel pipette.

For final vial sampling, units were reported in units/vial, where: units/vial=average units/mL×muvial.

If a specific activity was required for sterile bulk samples, the average of all five replicates in units/mg were reported, where:

$$^*\text{specific activity(units/mg)} = \frac{\text{units of activity mL}}{\text{mg of protein/mL}}$$

*Units/mL or units/mg may be converted to international units (IU)/mL or IU/mg by multiplication by the appropriate international unit conversion factor.

| Suggested Plate Map | | | | | | | | | |
|---|---|---|---|---|---|---|---|---|---|
| 200 ng Std | 400 ng Std | 600 ng Std | 800 ng Std | 1000 ng Std | Assay Dil | Assay Dil | Assay Dil | Assay Dil | Assay Dil |
| 200 ng Std | 400 ng Std | 600 ng Std | 800 ng Std | 1000 ng Std | Assay Dil | Assay Dil | Assay Dil | Assay Dil | Assay Dil |
| Control | Sample 1 | Sample 2 | Sample 3 | Sample 4 | Sample 5 | Sample 6 | Sample 7 | Sample 8 | Sample 9 |
| " | " | " | " | " | " | " | " | " | " |
| " | " | " | " | " | " | " | " | " | " |

The fibrinogen solution was allowed to reach room temperature prior to the addition of plasminogen. 200 μL per well of fibrinogen-plasminogen was added to the plate as rapidly as possible across the plate.

After the addition of fibrinogen-plasminogen, the plate was placed immediately into the plate reader and data collection was begun. The first reading was taken with two minutes of adding the fibrinogen-plasminogen to the plate, so that the maximal absorbance of the clot was recorded.

The absorbance of the plate at 340 nm was collected, and read at an appropriate time interval (usually 30 seconds) until baseline absorbance for all wells was achieved (usually one hour).

i. Calculation:

The endpoint determination (time to half-maximal lysis) was made as follows: Lysis times were calculated as the time for the absorbance to reach the half-maximal absorbance. The maximal absorbance corresponded to the maximal clot opacity recorded for that well. The background absorbance corresponded to the minimum absorbance of the totally lysed clot. The raw data points (lysis times in seconds) were averaged for each of the standard, control, and sample replicates. The log of the averaged value was calculated.

A standard curve was plotted by entering the data from lysis times (log seconds–y-axis) versus the rt-PA standard curve protein concentration (log ng/mL–x-axis).

Using the slope and intercept values obtained from the linear regression analysis, the log concentration was calculated for each sample from the log lysis time. The antilog of the obtained log concentration was taken and multiplied by the dilution factor (e.g., 1667) to obtain units/mL.

$$^*(\text{units/mL}) = \text{antilog}\left[\frac{[\log \text{lysis time} - y\text{-intercept}]}{[\text{slope}]}\right] \times \frac{1 \text{ mg}}{1{,}000{,}000 \text{ ng}} \times (\text{sample dilution}) \times (1 \text{ unit/mg}).$$

System suitability was determined. For a determination to be valid, the correlation coefficient for the standards must be between −0.995 and −1.000, and the control within ±10% of its accepted value. If system suitability was not met, the standard curve could be redefined by running the calculation program again using no fewer than four contiguous points (i.e., the first or last standard may be omitted).

The rt-PA activity was reported as units/vial, units/mg, units/mL, IU/vial, IU/mg, or IU/mL, as required on the assay data sheet. The assay may be repeated based on the results of the in-house control and/or based on determinate or indeterminate error. The final results may be reported as an average of multiple tests.

Results

By visual inspection the alteplase t-PA diluted to 0.01, 0.025, and 0.05 mg/mL with NS appeared as colorless, clear to slightly opalescent solutions initially and after 24 hours of infusion (with no filter) at room temperature. At 0.1 mg/mL in NS, alteplase t-PA appeared as a slightly cloudy solution immediately after dilution and remained as such throughout the infusion period.

In the majority of cases, all fractions collected over 24 hours for all concentrations demonstrated specific activities greater than 90% as assessed by the clot-lysis activity assay.

Conclusion

Recovered t-PA (5 mg/mL) diluted to 0.01, 0.02, and 0.05% mg/mL in 0.9% NaCl IV bags (500 mL) was lytically active after 24 hours of storage at ambient conditions.

EXAMPLE 8

Summary

Tenecteplase diluted down to 0.01 mg/mL in normal saline was found to be lytically active in a clot lysis effectiveness test. In such test, thrombin and fibrinogen are mixed together to produce fibrin; plasminogen and tenecteplase are mixed together to produce plasmin; and together the fibrin and plasmin lyse the clot. The test measures the effectiveness of tenecteplase to act with plasminogen to form plasmin and thus lyse the clot.

Materials and Methods

A. Materials and Chemicals
Teneteplase, TNKASE™, 50 mg vial
0.9% NaCl injection, USP, 500 mL (Baxter)
10 mL SWFI, USP (Abbott)
3-cc, 5-cc, and 10-cc BD syringes
22 G 1.5 needles
5-cc WHEATON™ Type I clear glass vials
20-mm gray butyl rubber liquid stoppers B. Methods Tenecteplase (TNKASE™ variant of t-PA), obtained from Genentech, Inc. (e.g., U.S. Pat. No. 5,612,029) (50 mg/vial) was reconstituted to 5 mg/mL with 10 mL of SWFI. Using a 3 & 5 cc syringe and 22 G needle, 1, 2, and 5 mL of normal saline (NS) was removed from separate IV bags (500 mL NS, Baxter), in duplicates. The same volume was replaced with the reconstituted drug product to give a final tenecteplase concentration inside the bags of 0.01, 0.02, and 0.05 mg/mL. The bags were then mixed gently by inversions. A 10-mL aliquot of the diluted tenecteplase solution was sampled via the IV port with a 10-cc syringe and dispensed into two 5-cc clean clear glass vials (6 mL in one and the remaining in the other). The IV bags containing the diluted tenecteplase were placed on a bench top under normal fluorescent light at ambient conditions for 24 hours. Additional aliquots (10 mL each) from these IV bags were sampled after 8 and 24 hours of storage.

C. Assays

The pH determination was performed using a RADIOMETER PHM 93™ pH meter and a microelectrode (MI-410™, Microelectrode, Inc.). The pH meter was standardized with pH 4.01 and 7.00 buffer standards prior to measurement at ambient conditions.

All the aliquots of tenecteplase were subjected to the clot lysis assay described above to determine the in vitro bioactivity of tenecteplase in these aliquots. The samples were diluted to two or three different concentrations within assay range (200-500 ng/mL) with the diluent. Tenecteplase was used as an internal reference. All values obtained were normalized to the tenecteplase reference material. The bioactivity was assayed by clot lysis before and after centrifugation.

Results

A summary of the results is shown in Table 26. The observed pH (7.1-7.2) for the higher tenecteplase concentration (0.05 mg/mL in NS) was slightly higher than that for the lower concentrations (pH 6.7-6.8 and pH 6.8-6.9 at 0.01 and 0.02 mg/mL, respectively). This is due to the larger amount of the buffered tenecteplase (5 mg/mL, pH 7.3) being added to the IV bag directly for initial dilution. But all the pH values remained unchanged after 24 hours of storage at ambient conditions.

The clot lysis activity and protein concentrations (determined by RP-HPLC) were performed before and after centrifugation of each sample aliquot. This was to ensure that any precipitation that was not visible to the naked eye was removed prior to assay for more accurate interpretation of the results. In all cases, the results after centrifugation were slightly lower for both activity and concentration than before centrifugation, suggesting a small amount of precipitation occurred. Table 26 shows the percent change in concentration before and after centrifugation, which indicates the loss of protein is higher at 0.01 and 0.02 mg/mL initially soon after dilution than at higher concentration (0.5 mg/mL). This percent change at lower concentration (0.01 mg/mL) also increased with time of storage. At 0.01 mg/mL, the percent change in concentration was 57% immediately after dilution and increased to 71% after 24 hours. No significant change was observed at 0.02 and 0.05 mg/mL. This observation can be explained, without being limited to any one theory, by a more pronounced protein adsorption at a lower concentration that usually occurs instantly and saturates with time.

Table 27 shows that the percent protein recovery relative to the targeted concentrations at 0.01, 0.02, and 0.05 mg/mL was 40-50%, 65%, and 86-92%, respectively. This percent recovery was under-estimated because the overfill volume inside the IV bag was not accounted for and the protein recovered would be at least 10% lower than the expected target concentrations (assuming 10% overfill in the IV bag).

The clot lysis activity of the recovered protein (after centrifugation) did not change significantly upon 24 hours of storage at ambient conditions. The overall percent specific activity of the recovered protein at 0.01, 0.02, and 0.05 mg/mL was ≧100%, ≧92%, and ≧80%, respectively (Table 27).

TABLE 26

Stability Summary of Tenecteplase Dilutions into 0.9% NaCl IV Bags (500 mL)

| Time | Targeted Conc.* (mg/mL) | pH | Clot lysis (−cent) (mg/mL) | Clot lysis (+cent) (mg/mL) | Conc.** (−cent) (mg/mL) | Conc.** (+cent) (mg/mL) | % Change in Conc. (±cent) |
|---|---|---|---|---|---|---|---|
| T = 0 | 0.01 | 6.70 | 0.006 | 0.004 | 0.007 | 0.004 | 57 |
| T = 0 | 0.01 | 6.73 | 0.006 | 0.004 | 0.007 | 0.004 | 57 |
| T = 0 | 0.02 | 6.83 | 0.015 | 0.012 | 0.017 | 0.013 | 76 |
| T = 0 | 0.02 | 6.93 | 0.015 | 0.012 | 0.017 | 0.013 | 76 |
| T = 0 | 0.05 | 7.12 | 0.040 | 0.037 | 0.048 | 0.045 | 94 |
| T = 0 | 0.05 | 7.15 | 0.041 | 0.036 | 0.047 | 0.046 | 98 |
| T = 8 hours ambient | 0.01 | — | 0.007 | 0.005 | 0.007 | 0.004 | 57 |
| T = 8 hours ambient | 0.01 | — | 0.008 | 0.006 | 0.008 | 0.005 | 63 |
| T = 8 hours ambient | 0.02 | — | 0.015 | 0.012 | 0.016 | 0.013 | 81 |

TABLE 26-continued

Stability Summary of Tenecteplase Dilutions into 0.9% NaCl IV Bags (500 mL)

| Time | Targeted Conc.* (mg/mL) | pH | Clot lysis (−cent) (mg/mL) | Clot lysis (+cent) (mg/mL) | Conc.** (−cent) (mg/mL) | Conc.** (+cent) (mg/mL) | % Change in Conc. (±cent) |
|---|---|---|---|---|---|---|---|
| T = 8 hours ambient | 0.02 | — | 0.013 | 0.012 | 0.016 | 0.013 | 81 |
| T = 8 hours ambient | 0.05 | — | 0.039 | 0.034 | 0.047 | 0.045 | 96 |
| T = 8 hours ambient | 0.05 | — | 0.039 | 0.037 | 0.047 | 0.045 | 96 |
| T = 24 hours ambient | 0.01 | 6.77 | 0.007 | 0.005 | 0.007 | 0.005 | 71 |
| T = 24 hours ambient | 0.01 | 6.71 | 0.007 | 0.006 | 0.007 | 0.005 | 71 |
| T = 24 hours ambient | 0.02 | 6.86 | 0.015 | 0.013 | 0.016 | 0.013 | 81 |
| T = 24 hours ambient | 0.02 | 6.90 | 0.016 | 0.012 | 0.016 | 0.013 | 81 |
| T = 24 hours ambient | 0.05 | 7.10 | 0.043 | 0.040 | 0.0480 | 0.043 | 90 |
| T = 24 hours ambient | 0.05 | 7.07 | 0.043 | 0.040 | 0.0460 | 0.044 | 96 |

*Targeted concentration. Overfill in IV bags was not accounted for.
**Concentration by RP-HPLC.
−cent = before centrifugation
+cent = after centrifugation

TABLE 27

Bioactivity, % Protein Recovery, and % Specific Activity of Diluted Tenecteplase Upon Storage

| Time | Conc.* (mg/mL) | Conc.** (+cent) (mg/mL) | % Protein Recovery (of targeted conc.) | Clot lysis (+cent) (mg/mL) | % Specific Activity |
|---|---|---|---|---|---|
| T = 0 | 0.01 | 0.004 | 40 | 0.004 | 100 |
| T = 0 | 0.01 | 0.004 | 40 | 0.004 | 100 |
| T = 0 | 0.02 | 0.013 | 65 | 0.012 | 92 |
| T = 0 | 0.02 | 0.013 | 65 | 0.012 | 92 |
| T = 0 | 0.05 | 0.045 | 90 | 0.037 | 82 |
| T = 0 | 0.05 | 0.046 | 92 | 0.036 | 78 |
| T = 8 hours ambient | 0.01 | 0.004 | 40 | 0.005 | 125 |
| T = 8 hours ambient | 0.01 | 0.005 | 50 | 0.006 | 120 |
| T = 8 hours ambient | 0.02 | 0.013 | 65 | 0.012 | 92 |
| T = 8 hours ambient | 0.02 | 0.013 | 65 | 0.012 | 92 |
| T = 8 hours ambient | 0.05 | 0.045 | 90 | 0.034 | 76 |
| T = 8 hours ambient | 0.05 | 0.045 | 90 | 0.037 | 82 |
| T = 24 hours ambient | 0.01 | 0.005 | 50 | 0.005 | 100 |
| T = 24 hours ambient | 0.01 | 0.005 | 50 | 0.006 | 120 |
| T = 24 hours ambient | 0.02 | 0.013 | 65 | 0.013 | 100 |
| T = 24 hours ambient | 0.02 | 0.013 | 65 | 0.012 | 92 |
| T = 24 hours ambient | 0.05 | 0.043 | 86 | 0.040 | 93 |
| T = 24 hours ambient | 0.05 | 0.044 | 88 | 0.040 | 91 |

*Targeted concentration. Overfill in IV bags was not accounted for.
**Concentration by RP-HPLC
+cent = after centrifugation
% Protein recovery = [Conc. (+cent), mg/mL/Targeted conc., mg/mL] × 100%
% Specific Activity = [Clot lysis (+cent), mg/mL/Conc. (+cent), mg/mL] × 100%

Conclusion

As with t-PA as noted above, recovered tenecteplase (5 mg/mL) diluted to 0.01, 0.02, and 0.05% mg/mL in 0.9% NaCl IV bags (500 mL) was lytically active after 24 hours of storage at ambient conditions.

The aforedescribed compositions and preparations are expected to be effective in preventing the adherence and colonization of catheter surfaces by infectious organisms such as *S. aureus, S. epidermidis,* and fungi.

What is claimed is:

1. A method for removing fibrin-bound blood clots from a catheter that contains such blood clots comprising contacting the catheter for at least about 5 days with a composition comprising water, a fibrinolytically effective amount of a tissue-plasminogen activator in a native form (t-PA) or in a variant form selected from group consisting of reteplase and tenecteplase, and a preservatively effective amount of a bacteriostatic organic alcohol, wherein the composition does not comprise a chelating agent.

2. The method of claim 1 wherein the catheter is contacted with the composition for about 6 to 15 days.

3. The method of claim 1 wherein the tissue-plasminogen activator is in the native form (t-PA).

4. The method of claim 1 wherein the organic alcohol is benzyl alcohol.

5. The method of claim 1 wherein the fibrinolytically effective amount of tissue-plasminogen activator is from about 0.1 to 10 mg/mL and the preservatively effective amount of organic alcohol is from about 0.5 to 1.2% (v/v).

6. The method of claim 5 wherein the fibrinolytically effective amount of tissue-plasminogen activator is from about 0.3 to 4 mg/mL.

7. The method of claim 1 wherein the water in the composition is bacteriostatic water for injection or bacteriostatic normal saline.

* * * * *